(12) United States Patent
Matula et al.

(10) Patent No.: US 7,976,598 B2
(45) Date of Patent: Jul. 12, 2011

(54) MULTI-FLOW FILTRATION SYSTEM

(75) Inventors: Paul A. Matula, Brookfield, CT (US); Dominick Mastri, Bridgeport, CT (US); James R. Parys, Wallingford, CT (US); Ralph Stearns, Bozrah, CT (US); Johnnie H. Copley, Morris, IL (US); Christopher Estkowski, Pullman, MI (US)

(73) Assignee: SurgiQuest, Inc., Orange, CT (US)

( * ) Notice: Subject to any disclaimer, the term of this patent is extended or adjusted under 35 U.S.C. 154(b) by 61 days.

(21) Appl. No.: 12/577,188

(22) Filed: Oct. 11, 2009

(65) Prior Publication Data

US 2010/0170208 A1  Jul. 8, 2010

Related U.S. Application Data

(63) Continuation of application No. PCT/JP2009/060298, filed on Oct. 10, 2009.

(60) Provisional application No. 61/195,898, filed on Oct. 10, 2008.

(51) Int. Cl.
*B01D 45/00* (2006.01)

(52) U.S. Cl. ............. 55/344; 55/345; 55/350.1; 55/498; 55/342; 55/495; 55/343; 210/295; 210/323.1; 210/323.2; 210/435; 210/438

(58) Field of Classification Search .................... 55/344, 55/350.1, 498, 342, 495, 343; 210/295, 323.1, 210/323.2, 435, 438
See application file for complete search history.

(56) References Cited

U.S. PATENT DOCUMENTS

| | | | |
|---|---|---|---|
| 6,068,762 A | 5/2000 | Stone et al. | |
| 6,787,033 B2 * | 9/2004 | Beard et al. | 210/323.2 |
| 6,942,797 B1 | 9/2005 | Chancellor et al. | |
| 7,837,754 B2 * | 11/2010 | Johnson et al. | 55/482 |
| 2003/0019807 A1 * | 1/2003 | Beard et al. | 210/323.2 |
| 2003/0196948 A1 | 10/2003 | Bassett et al. | |
| 2006/0130445 A1 * | 6/2006 | Park et al. | 55/346 |
| 2006/0283160 A1 | 12/2006 | Johnson et al. | |

OTHER PUBLICATIONS

International Search Report dated May 27, 2010 in corresponding PCT Application.

* cited by examiner

*Primary Examiner* — Jason M Greene
*Assistant Examiner* — Dung H Bui
(74) *Attorney, Agent, or Firm* — Scott D. Wofsy; Brian R. Pollack; Edwards Angell Palmer & Dodge LLP

(57) ABSTRACT

Disclosed is multi-flow filter cartridge assembly that includes an elongated housing that has axially opposed proximal and distal ends and defines an interior cavity and first, second and third flow paths which extend from the proximal end of the housing to the distal end. The cartridge assembly also includes first, second and third filter elements. The first filter element is disposed within the interior cavity of the housing and conditions fluid that traverses the first flow path from a first inlet port to a first outlet port. The second filter element is disposed within the interior cavity of the housing and conditions fluid that traverses the second flow path from a second inlet port to a second outlet port. Lastly, the third filter element is also disposed within the interior cavity of the housing and conditions fluid that traverses the third flow path from a third inlet port to a third outlet port. The first flow path is isolated from the second and third flow paths and the second flow path is isolated from the third flow path.

72 Claims, 24 Drawing Sheets

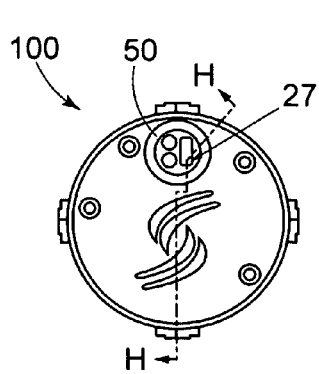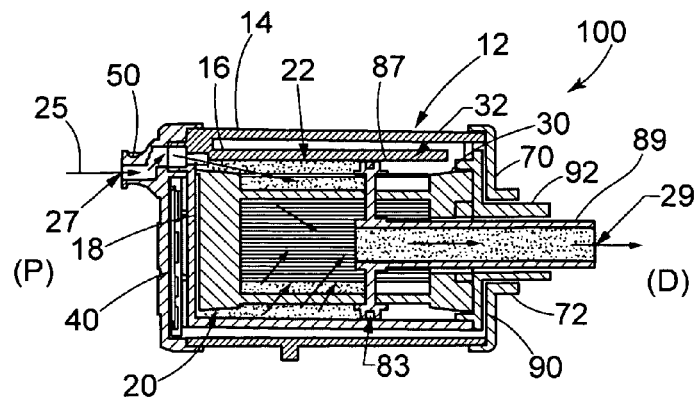
Fig. 3A  Fig. 3B
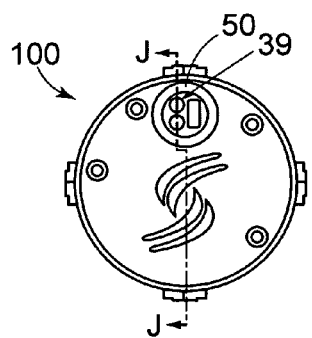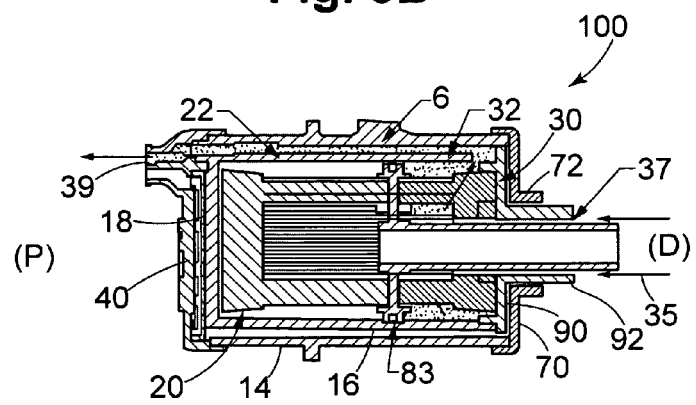
Fig. 4A  Fig. 4B
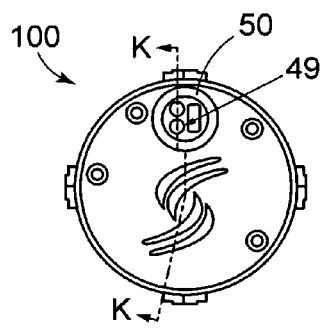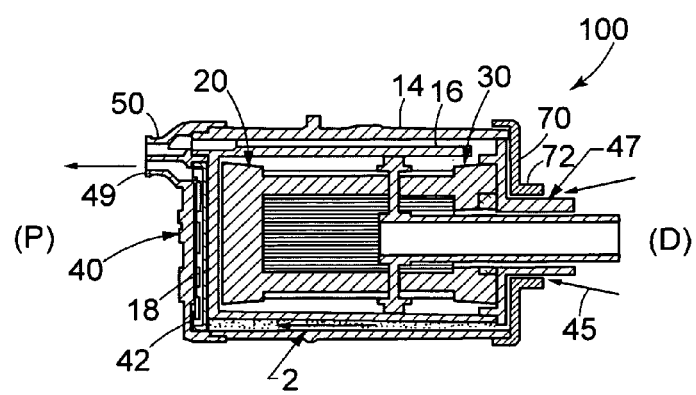
Fig. 5A  Fig. 5B

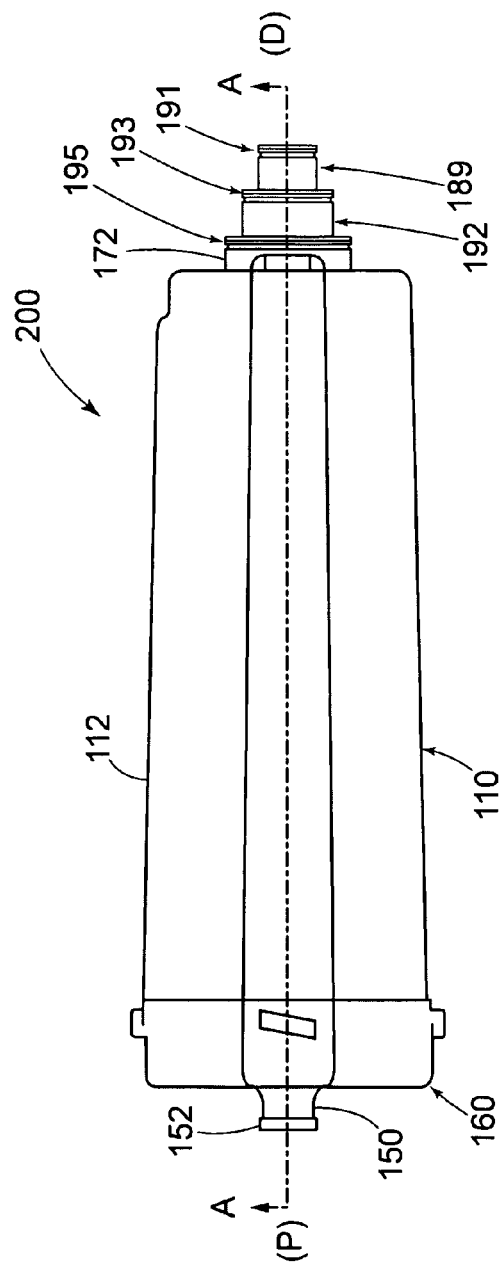
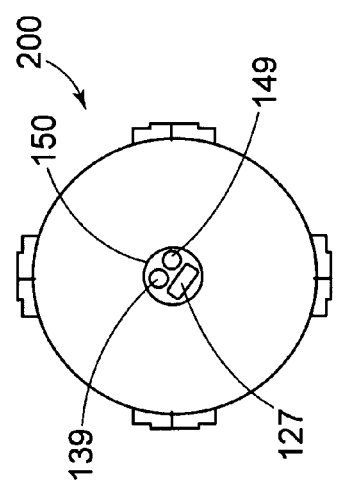
Fig. 9A
Fig. 9B

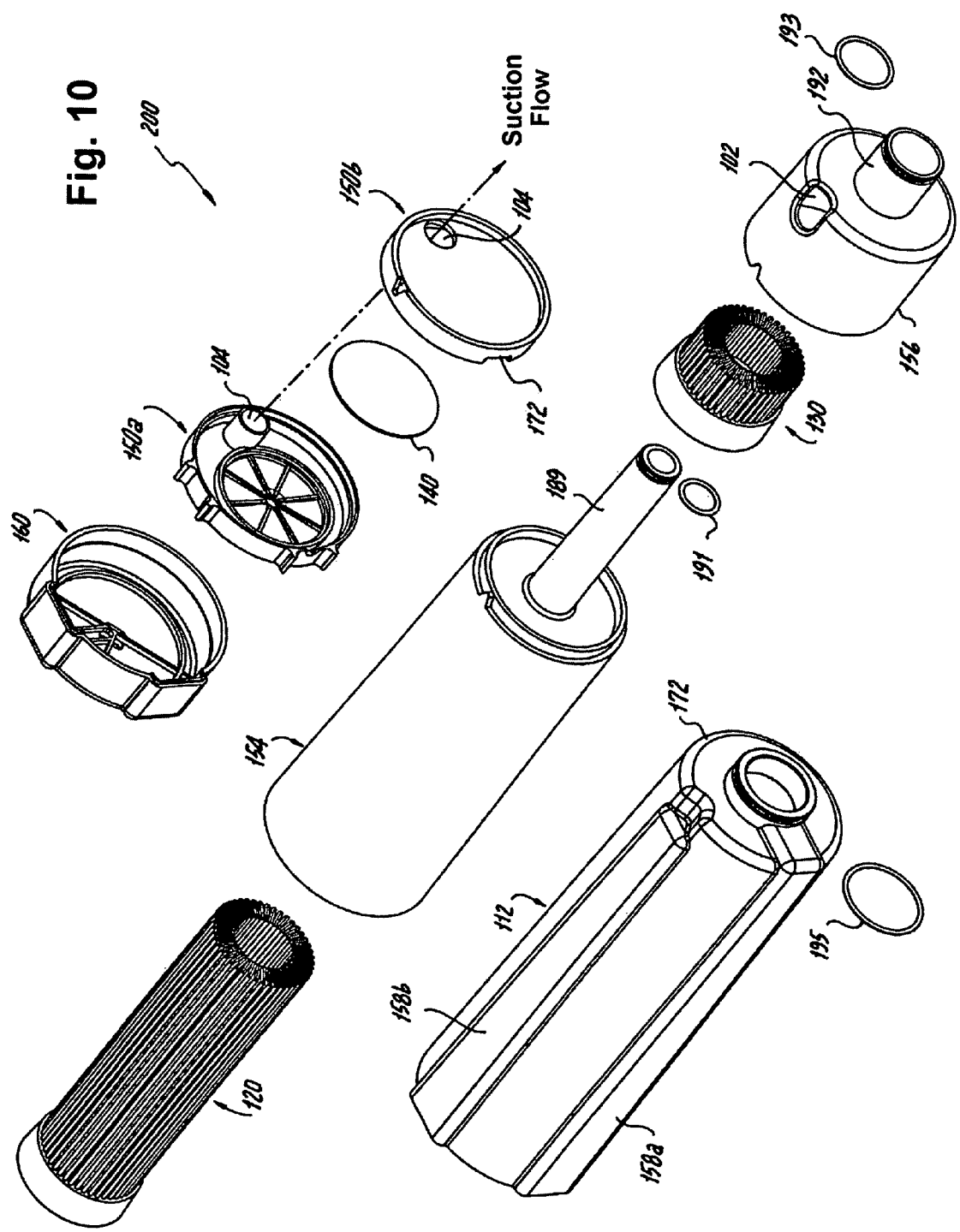

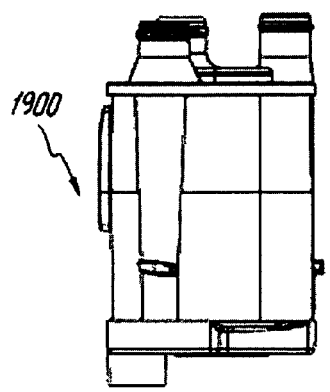
Fig. 21
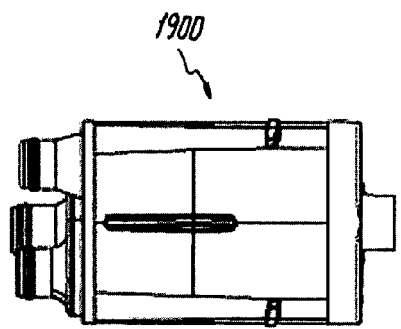 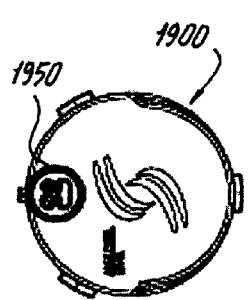 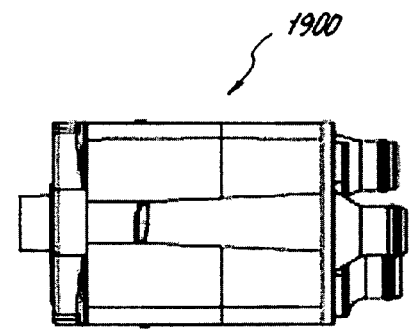
Fig. 22     Fig. 23     Fig. 24
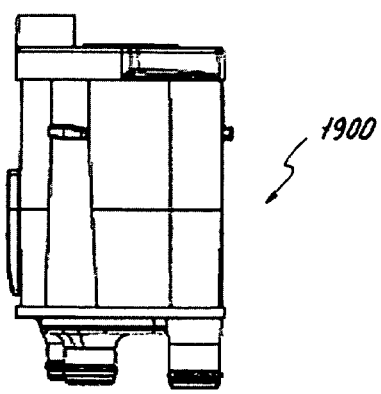
Fig. 25

MULTI-FLOW FILTRATION SYSTEM

CROSS-REFERENCE TO RELATED APPLICATIONS

This application is a continuation application of PCT application serial number PCT/US2009/060298, filed Oct. 10, 2009, which claims the benefit of priority to U.S. Patent Application Ser. No. 61/195,898, filed Oct. 10, 2008. Each of the aforementioned applications is incorporated herein by reference in its entirety.

BACKGROUND OF THE INVENTION

1. Field of the Invention

The present invention is directed to a filtration system for use in, for example, healthcare applications, and more particularly to a filtration system that includes a filter cartridge assembly having a plurality of distinct fluid flow paths and filter chambers, and still more particularly to, a filtration system that includes a tri-flow filter cartridge assembly and a controller which are adapted and configured for filtering or conditioning three independent fluid sources.

2. Background of the Related Art

Many applications, such as healthcare, residential, or industrial applications, require a fluid or gas source to be filtered prior to use. For example, in laparoscopic procedures the abdominal cavity of the patient is filled or insufflated with a pressurized fluid, such as carbon dioxide gas, to create what is referred to as pneumoperitoneum. The carbon dioxide gas must be filtered prior to its being supplied to the patient's abdominal cavity.

Still further, many applications require the filtration of more than one fluid source. For example, International Patent Application No. PCT/US07/88017 which was filed on Dec. 18, 2007 and published as WO 2008/077080 and is incorporated herein by reference in its entirety, discloses a system for surgical insufflation and gas recirculation to be used in laparoscopic procedures that utilizes three independent fluid streams, which are filtered during use. FIGS. 14 and 15 of WO 2008/077080, disclose a representative system for surgical insufflation and gas recirculation that includes, among other elements, a control unit in connection with a surgical insufflator and a surgical trocar. In the disclosed system, three fluid conduits connect the trocar to the control unit. A separate filter element is provided in each of the three flow paths extending between the control unit and the trocar. The use of three separate filter elements with three filter housings is cumbersome and not desirable in an operating room setting where space is at a premium. Moreover, although the filter elements appear to be identical, in fact, the size and type of filter cartridge used will vary depending on the desired flow properties and conditioning requirements for each flow path. Therefore, there is a possibility that during maintenance procedures, the filter cartridges could be mixed up and improperly placed in wrong housing and flow path. Additionally, when the filters need to be replaced, which in a laparoscopic procedure will be before each surgery, each filter cartridge must be separately removed from within its housing and replaced, which adds to the scope of the maintenance efforts.

There is a need therefore, for a filter cartridge assembly for use in applications such as laparoscopic surgery that is adapted and configured for filtering three independent fluid sources. Additionally, there is also a need for a filtration system that can be used in a surgical environment which is compact and simple to use and maintain.

SUMMARY OF THE INVENTION

The present invention is directed to a filter cartridge assembly that includes, inter alia, an elongated housing that has axially opposed proximal and distal ends and defines an interior cavity and first, second and third flow paths which extend from the proximal end of the housing to the distal end.

The cartridge assembly also includes first, second and third filter elements. The first filter element is disposed within the interior cavity of the housing and conditions fluid that traverses the first flow path from a first inlet port to a first outlet port. The second filter element is disposed within the interior cavity of the housing and conditions fluid that traverses the second flow path from a second inlet port to a second outlet port. Lastly, the third filter element is also disposed within the interior cavity of the housing and conditions fluid that traverses the third flow path from a third inlet port to a third outlet port. The first flow path is isolated from the second and third flow paths and the second flow path is isolated from the third flow path.

Preferably, the proximal end of the housing includes a connector element. In certain embodiments of the present invention, the connector element includes the first inlet port and the second and third outlet ports.

It is envisioned that the housing includes a pair of coaxially positioned peripheral walls. In certain constructions, the peripheral walls of the housing are integrally molded. In alternative constructions, the inner peripheral wall is formed using a cylindrical inner housing element positioned within the interior cavity of the housing. It is envisioned that in such constructions a portion of the second and third flow paths extend in a gap defined between the peripheral walls of the housing.

It is presently preferred that the first filter element is a radially pleated filter and fluid is conditioned in the first flow path by traversing in a radially inward direction through the first filter element. Moreover, it is also envisioned that the second filter element is radially pleated filter and fluid is conditioned in the second flow path by traversing in a radially outward direction through the second filter element. Lastly, in preferred embodiments of the present invention, the third filter element is a disc filter and fluid is conditioned in the second flow path by traversing axially through the third filter element.

In certain constructions of the presently disclosed filter cartridge assembly, the housing further includes a second inner housing element positioned within the interior cavity of the housing and forming a second filter chamber for the second filter element. Still further, it is envisioned that in an embodiment of the present invention, the housing includes two longitudinal ribs which define two longitudinal channels in the interior cavity of the housing and the second flow path extends through one of the channels and the third flow path extends though the other channel.

Preferably, the first outlet port, the second inlet port and third inlet port are located at the distal end of the housing. Still further, it is envisioned that the first outlet port, the second inlet port and the third inlet port can be coaxially arranged.

The present invention is also directed to a filter cartridge assembly that includes, inter alia, an elongated housing that has axially opposed proximal and distal ends. The housing defines first, second and third filter chambers and first, second and third flow paths which extend from the proximal end of the housing to the distal end. A first filter element is disposed within the first filter chamber of the housing and conditions fluid that traverses the first flow path from a first inlet port to a first outlet port. A second filter element is disposed within the second filter chamber of the housing and conditions fluid that traverses the second flow path from a second inlet port to a second outlet port. A third filter element is disposed within the third filter chamber of the housing and conditions fluid that traverses the third flow path from a third inlet port to a third outlet port. The cartridge assembly is constructed such that the first flow path is isolated from the second and third flow paths and the second flow path is isolated from the third flow path.

The present invention is also directed to a filter cartridge assembly that includes, among other elements, an elongated housing that has a central axis and axially opposed proximal and distal ends. The housing defines a plurality of axially spaced apart filter chambers and a plurality of flow paths which extend from the proximal end of the housing to the distal end. The plurality of flow paths are each isolated from one another. The filter cartridge also includes a plurality of filter elements, and one of the plurality of filter elements is disposed within each of the plurality of filter chambers.

In a preferred embodiment, the housing defines three filter chambers and three flow paths. Still further, in such an embodiment it is envisioned that the plurality of filter elements includes a first filter element, a second filter element and a third filter element. The first filter element is disposed within the first filter chamber of the housing and conditions fluid traversing the first flow path from a first inlet port to a first outlet port. The second filter element is disposed within the second filter chamber of the housing and conditions fluid traversing the second flow path from a second inlet port to a second outlet port. The third filter element is disposed within the third filter chamber of the housing and conditions fluid traversing the third flow path from a third inlet port to a third outlet port.

The present invention is also directed to a filtration system for conditioning fluid received from three distinct fluid sources, the filtration system including, inter alia, a controller, a socket assembly and a filter cartridge assembly. The controller includes means for regulating and monitoring fluid flow in the filtration system and defines an elongated receptacle. The socket assembly is positioned at least partially within an elongated receptacle defined by the controller and includes a locking element. The filter cartridge assembly is inserted into the socket assembly and is secured in fluid communication with the controller by the locking element.

In a preferred embodiment of the present invention, the locking element of the socket assembly includes a cam mechanism for engaging one or more lugs extending from an exterior surface of the filter cartridge assembly.

It is presently envisioned that the filter cartridge assembly includes an elongated housing and first, second and third filter elements. The elongated housing has axially opposed proximal and distal ends and defines an interior cavity and first, second and third flow paths which extend from the proximal end of the housing to the distal end. The first filter element is disposed within the interior cavity of the housing and conditions fluid traversing the first flow path from a first inlet port to a first outlet port. The second filter element is disposed within the interior cavity of the housing and conditions fluid traversing the second flow path from a second inlet port to a second outlet port. The third filter element is disposed within the interior cavity of the housing and conditions fluid traversing the third flow path from a third inlet port to a third outlet port. The first flow path is isolated from the second and third flow paths and the second flow path is isolated from the third flow path.

BRIEF DESCRIPTION OF THE DRAWINGS

So that those having ordinary skill in the art will better understand the device and methods of the subject invention, embodiments thereof will be described below with reference to the drawings wherein:

FIGS. 3A and 3B provide elevational view and cross-sectional views, respectively, of the filter cartridge assembly of FIG. 1A, which illustrate a first flow path through the filter housing;

FIGS. 4A and 4B provide elevational view and cross-sectional views, respectively, of the filter cartridge assembly of FIG. 1A, which illustrate a second flow path through the filter housing;

FIGS. 5A and 5B provide elevational view and cross-sectional views, respectively, of the filter cartridge assembly of FIG. 1A, which illustrate a third flow path through the filter housing;

FIG. 9A is a side elevational view of a filter cartridge assembly constructed in accordance with a second preferred embodiment of the present invention;

FIG. 9B provides an elevational view of the proximal end of the filter cartridge assembly of FIG. 9A;

FIG. 10 is an exploded perspective view of the filter cartridge assembly of FIG. 9A shown with parts separated for ease of illustration;

FIG. 21 is a right side elevational view of the filter cartridge assembly of FIG. 19;

FIG. 22 is a top view of the filter cartridge assembly of FIG. 19;

FIG. 23 is a front view of the filter cartridge assembly of FIG. 19;

FIG. 24 is a bottom view of the filter cartridge assembly of FIG. 19;

FIG. 25 is a left side elevational view of the filter cartridge assembly of FIG. 19;

Figures 1A, 1B:
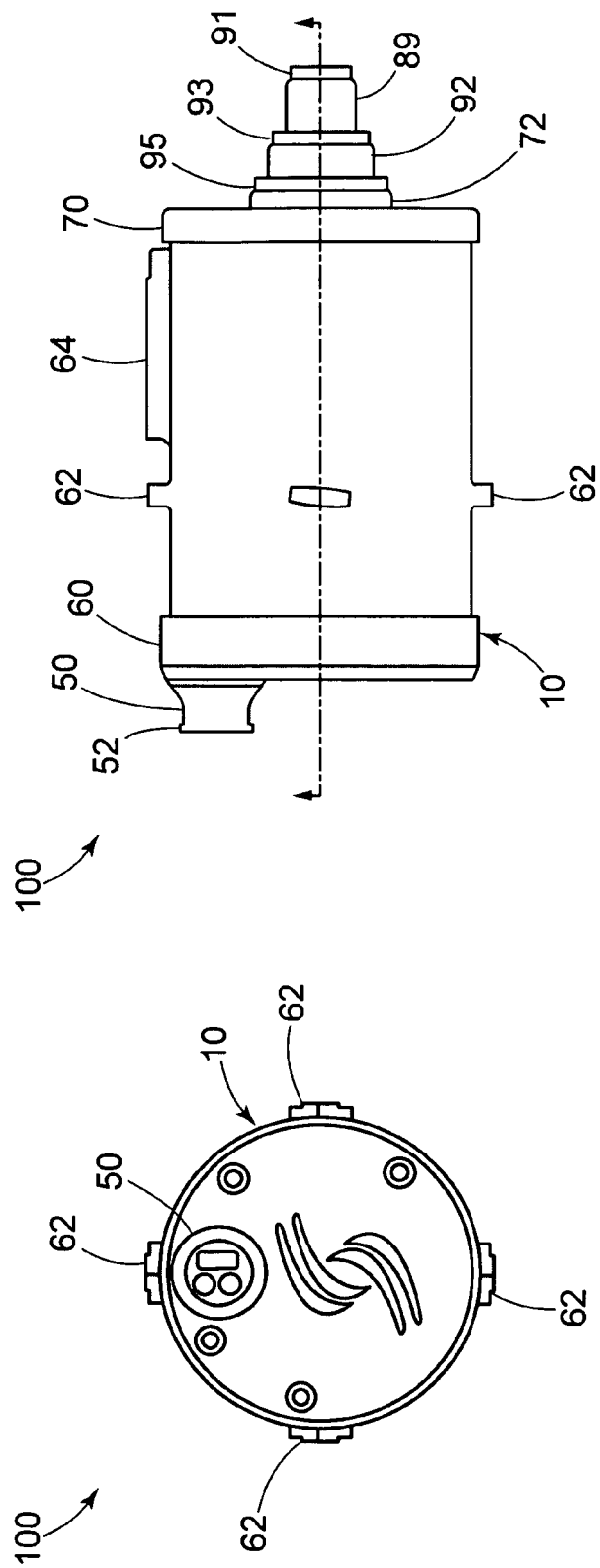
FIG. 1A is a side elevational view of a filter cartridge assembly constructed in accordance with the present invention.
FIG. 1B provides elevational view of the proximal end of the filter cartridge assembly of FIG. 1A.

The advantages of filter cartridge assemblies and filtration systems constructed in accordance with the present invention will become more readily apparent to those having ordinary skill in the art from the following detailed description of certain preferred and exemplary embodiments taken in conjunction with the drawings which set forth representative embodiments thereof, but are not intended to limit the scope of the present invention.

DETAILED DESCRIPTION OF THE PREFERRED EMBODIMENTS

Referring now to the drawings, wherein like reference numerals identify similar structural elements of the subject invention, there is illustrated in FIGS. 1A-8C a filter cartridge constructed in accordance with a preferred embodiment of the present invention and designated generally by reference numeral 100. Filter cartridge 100 includes an elongated housing 10 that has axially opposed proximal (P) and distal (D) ends and defines an interior cavity. As will be discussed in more detail hereinbelow, first, second and third flow paths, 25, 35 and 45 respectively, extend from the proximal end (P) of the housing to the distal end (D). The flow paths are illustrated with flow arrows in FIGS. 3B, 4B, 5B and 8A-8C.

Disposed within the interior cavity of filter cartridge 100 are first, second and third filter elements, 20, 30 and 40, respectively. The first filter element 20 conditions fluid that traverses the first flow path 25 from a first inlet port 27 (referred to in FIGS. 3A and 3B as the "suction connection slot") to a first outlet port 29 (referred to in FIG. 3B as the "suction/return connection port"). The second filter element 30 conditions fluid that traverses the second flow path 35 from a second inlet port 37 (referred to in FIG. 4B as the "pressure connection port at recirculation filtration pump") to a second outlet port 39 (referred to in FIG. 4A as the "pressure connection port"). Lastly, the third filter element conditions fluid that traverses the third flow path 45 from a third inlet port 47 (referred to in FIG. 5B as the "sense/insufflation connection port at recirculation filtration pump") to a third outlet port 49 (referred to in FIG. 5A as the "sense/insufflation connection port"). As best shown in FIGS. 3B, 4B and 5B, the first flow path 25 is isolated from the second and third flow paths, 35 and 45 respectively, and the second flow path 35 is isolated from the third flow path 45.

Figure 2:
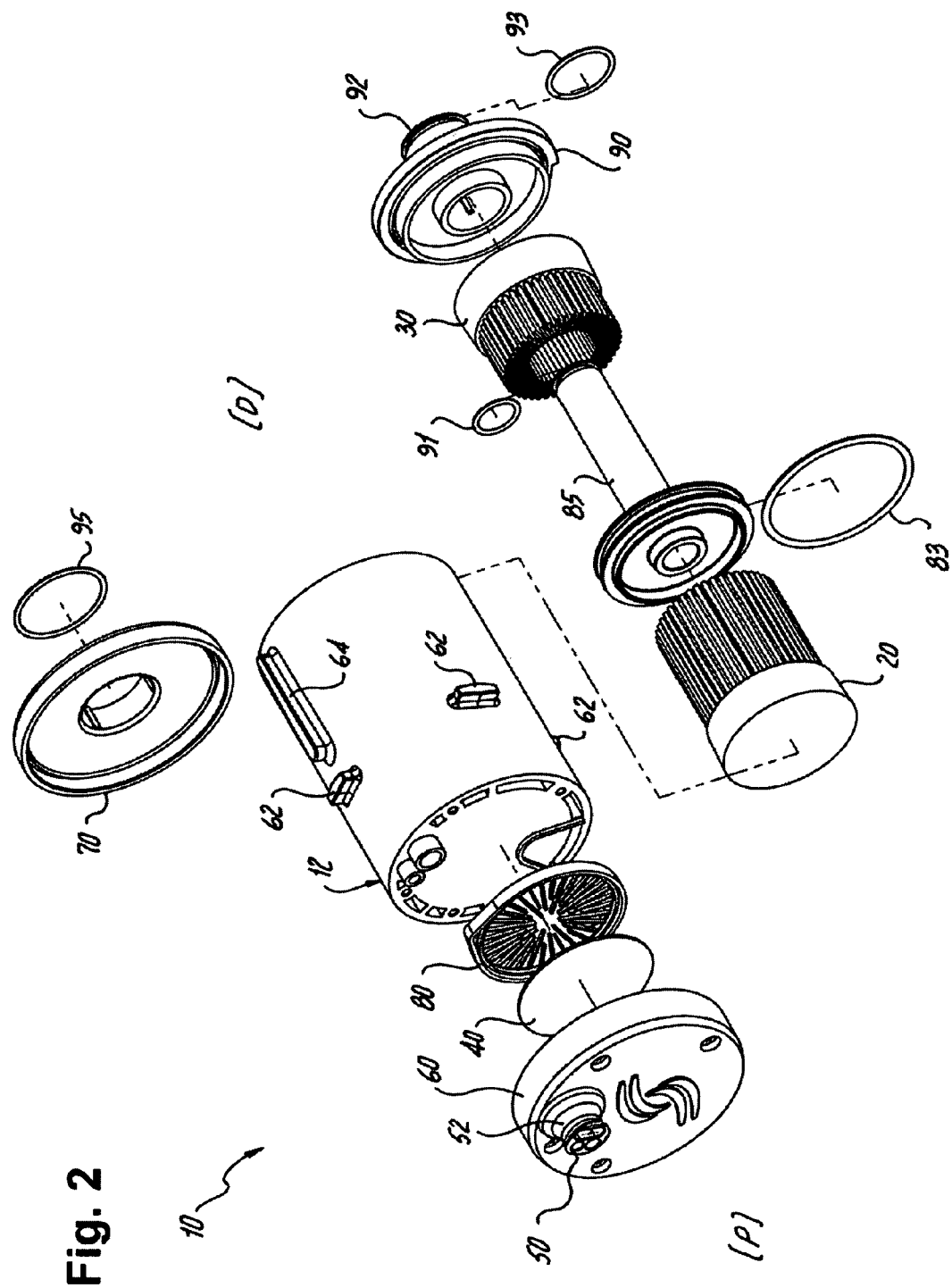
FIG. 2 is an exploded perspective view of the filter cartridge assembly of FIG. 1A shown with parts separated for ease of illustration.
Figure 6:
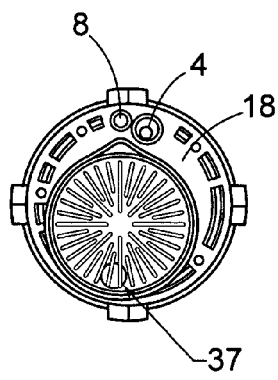
FIG. 6 provides an elevational view of the proximal end of the filter cartridge assembly of FIG. 1A, wherein the end cap and disc filter have been removed and the disc holder is exposed.
Figure 7:
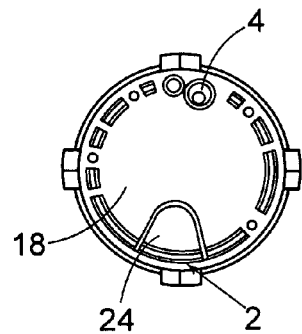
FIG. 7 provides an elevational view of the proximal end of the filter cartridge assembly of FIG. 1A, wherein the end cap, disc filter and disc holder have been removed and the flow passages are exposed.

As shown in FIGS. 2 and 3B, the first filter element 20 is a radially pleated filter. Fluid is conditioned in the first flow path 25 by traversing in a radially inward direction through the first filter element 20. As shown in FIGS. 2 and 4B, the second filter element 30 is also a radially pleated filter and fluid is conditioned in the second flow path 35 by traversing in a radially outward direction through the second filter element 30. Lastly, as shown in FIGS. 2 and 5A, the third filter element 40 is disc filter and fluid is conditioned in the second flow path 45 by traversing axially/proximally through the third filter element 40.

FIG. 2 provides an exploded perspective view of filter cartridge 100. As shown therein, housing 10 of the filter cartridge includes a main body portion 12, a proximal end cap 60 and a distal end cap 70. The main body portion 12 of the housing 10 partially defines the filter chambers for the first and second filter elements, 20 and 30 (see FIG. 3B). The first filter element 20 is inserted into the main body portion 12 and contacts proximal end wall 18. An internal filter support structure 85 (FIG. 2) sandwiches the first filter element 20 within a first sealed filter chamber 22 (identified in FIGS. 3B and 4B as the "suction filter chamber"). The internal filter support structure 85 includes a first partition element 87 which abuts the first filter element 20 and a cylindrical stem 89 which extends axially from the partition element 87. An O-ring 83 is positioned within a circumferential groove formed in the partition element 87 and aids in fluidly isolating the first filter chamber 22 from the second filter chamber 32.

The second filter element 30 is positioned over the cylindrical stem 89 of filter support structure 85 and a second partition element 90 is used to seal the distal end of the second filter chamber 32 (identified in FIGS. 3B and 3A as "the pressure filter chamber"). The second partition element 90 has a cylindrical neck portion 92 into which the cylindrical stem 89 of the filter support structure 85 is inserted.

The third filter element 40 is supported within the housing 10 on a disc holder 80. The third filter element 40 and the disc holder 80 are positioned between the proximal end cap 60 and the proximal end wall 18 of the main body portion 12 of housing 10.

As best shown in FIGS. 3B, 4B and 5B, the main body portion 12 of housing 10 includes a pair of coaxially positioned peripheral walls, 14 (outer) and 16 (inner), which are integrally molded with the proximal end wall 18. As shown in these figure and to be discussed in detail hereinbelow, a portion of the second and third flow paths, 35 and 45, extend in a passage defined between the peripheral walls of the housing 10.

Referring again to FIGS. 2, 3A, 4A and 5A, the proximal end (P) of the housing 10 includes a connector element 50. The connector element 50 houses the first inlet port 27 and the second and third outlet ports, 39 and 49, respectively. The connector element 50 also includes a male thread 52, similar to a luer lock fitting, which allows the filter cartridge 100 to be fluidly engaged with a tube set, for example, having a mating connector head. As best shown in FIGS. 3B, 4B and 5B, the first outlet port 29, the second inlet port 37 and third inlet port 47 are coaxially arranged at the distal end (D) of the housing 10.

As best shown in FIGS. 3A and 3B, the first flow path 25 extends from the first inlet port 27, a slotted hole formed in connector element 50, through an aperture 4 (see FIGS. 6 and 7) formed in the proximal end wall 18 of the main body portion 12 of housing 10 and into the first filter chamber 22. Then fluid in the first flow path 25 is distributed around the circumference of the first filter element 20 and is conditioned by passing in a radially inward direction (see FIG. 8C) through the filter media to the central core of the filter element. The conditioned fluid then travels distally from the central core of the first filer element 20 into the bore defined in the cylindrical stem 89 of the filter support structure 85 and exits the filter housing 10 through the first outlet port 29.

Figure 8A:
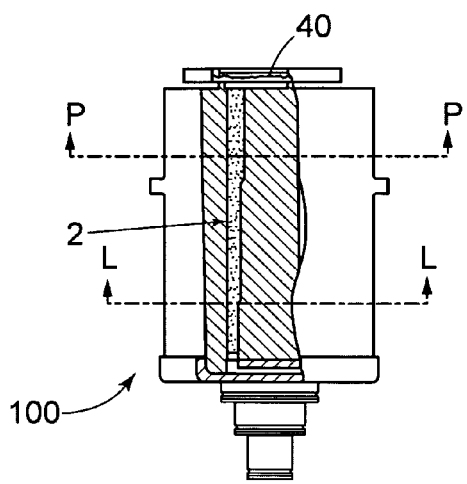
FIG. 8A is a partial cross-sectional view of the filter cartridge assembly of FIG. 1A shown with the proximal end cap removed and illustrating the third flow path.
Figure 8B:
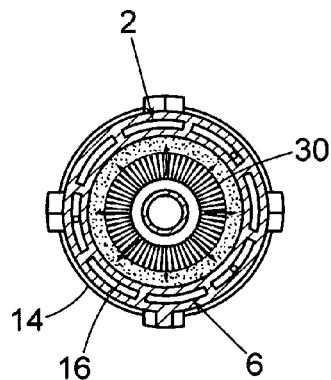
FIG. 8B is a cross-sectional view of the filter cartridge assembly of FIG. 1A taken along cut line L-L in FIG. 8A.

As best shown in FIGS. 4A and 4B, the second flow path 35 extends from the second inlet port 37 defined between the outer periphery of the cylindrical stem 89 of the filter support structure 85 and the cylindrical neck 92 of the second partition element 90 until it reaches the central core of the second filter element 30. Then the fluid in the second flow path is conditioned by proceeding in a radially outward direction through the filter media of the second filter element 30 (see FIG. 8B) and the conditioned fluid is supplied to an axial flow passage 6 defined between the inner 16 and outer peripheral walls 14 of the main body portion 12 of housing 10. The axial flow passage 6 is also shown in FIG. 8B and identified as the "pressure filter passage thru filter housing". The conditioned fluid in axially flow passage 6 exits the main body portion 12 of the housing 10 through a flow aperture 8 formed in peripheral end wall 18 (see FIG. 6) and exits the proximal end (P) of the filter cartridge 100 through the second outlet port 39 formed in connector 50.

Figure 8C:
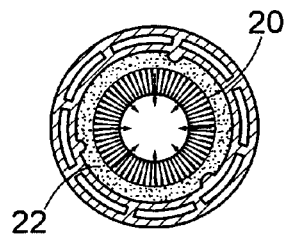
FIG. 8C is a cross-sectional view of the filter cartridge assembly of FIG. 1A taken along cut line P-P in FIG. 8A.

As best shown in FIGS. 5A and 5B, the third flow path 45 initially extends axially from the third inlet port 47, which is defined between the outer periphery of the cylindrical neck 92 of the second partition element 90 and the cylindrical neck 72 of the end cap 70, to a planar chamber defined between the end cap 70 and the second partition element 90. From this chamber the third flow path 45 proceeds radially outward to a second axial flow passage 2 defined between the inner 16 and outer 14 peripheral walls of the main body portion 12 of the housing 10. This axial flow passage 2 is also illustrated in FIGS. 8B and 8C (identified as the "sense/insufflation filter passage thru filter housing"). The fluid in the second axially flow passage 2 exits the main body portion of the housing through the peripheral end wall 18 and is supplied to a triangularly-shaped chamber 24 (see FIG. 7). From this chamber 24 the third flow path 45 proceeds through an aperture 37 formed in the disc holder 80 and through the third filter element 40, a disc filter. The conditioned fluid then exits the housing 10 through the third outlet port 49 formed in connector.

Referring now to FIGS. 9A-12B, there is illustrated a filter cartridge which has been constructed in accordance with a further preferred embodiment of the present invention and is designated generally by reference numeral 200. Filter cartridge 200 includes an elongated housing 110 that has axially opposed proximal (P) and distal (D) ends and defines an interior cavity. As will be discussed in more detail hereinbelow, first, second and third flow paths, 125, 135 and 145 respectively, extend from the proximal end (P) of the housing to the distal end (D). The flow paths are illustrated with flow arrows in FIGS. 11, 12A and 12B.

Figure 11:
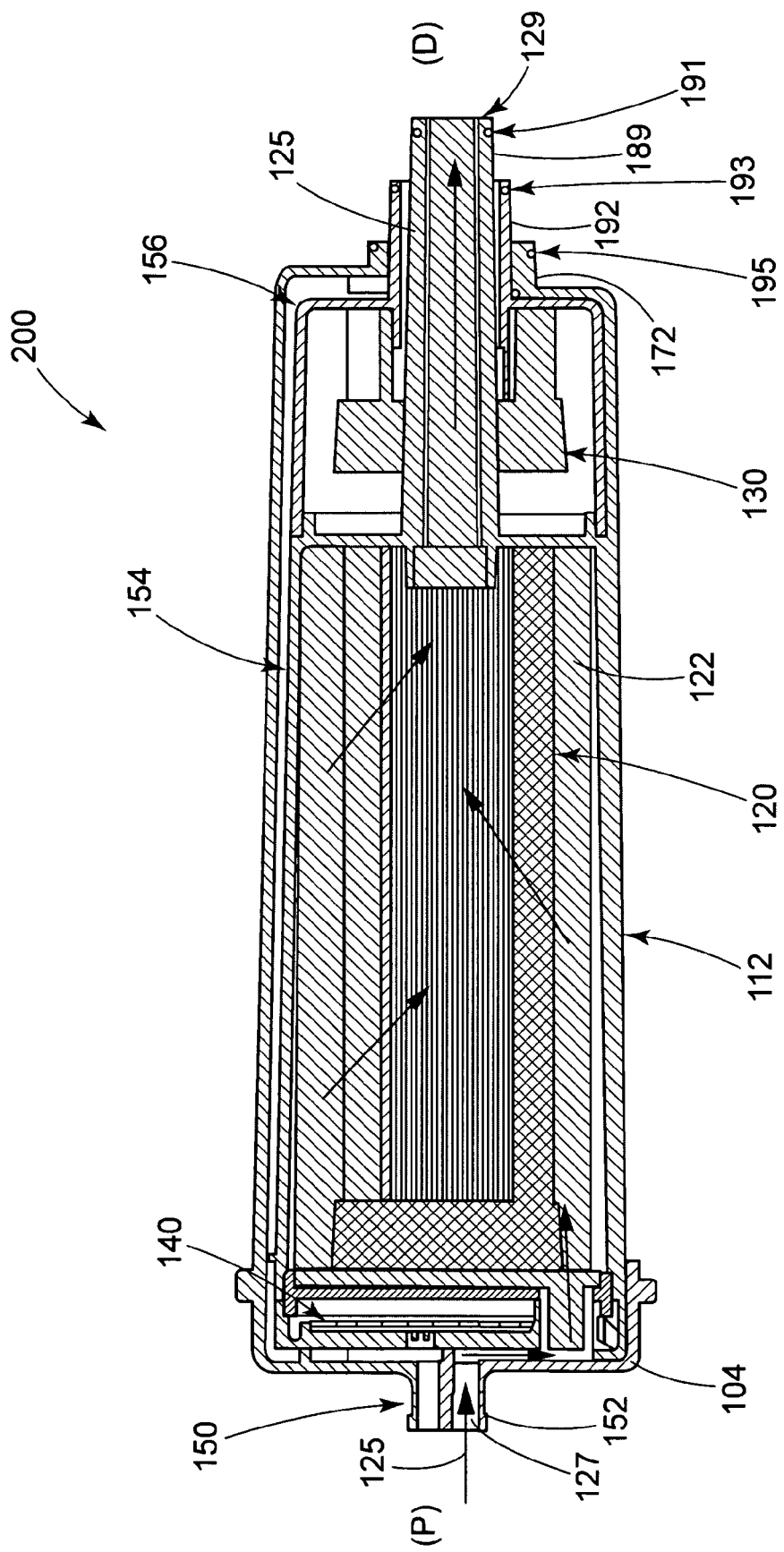
FIG. 11 is a cross-sectional view of the filter cartridge assembly of FIG. 9A which illustrates a first flow path through the filter housing.
Figure 12A:
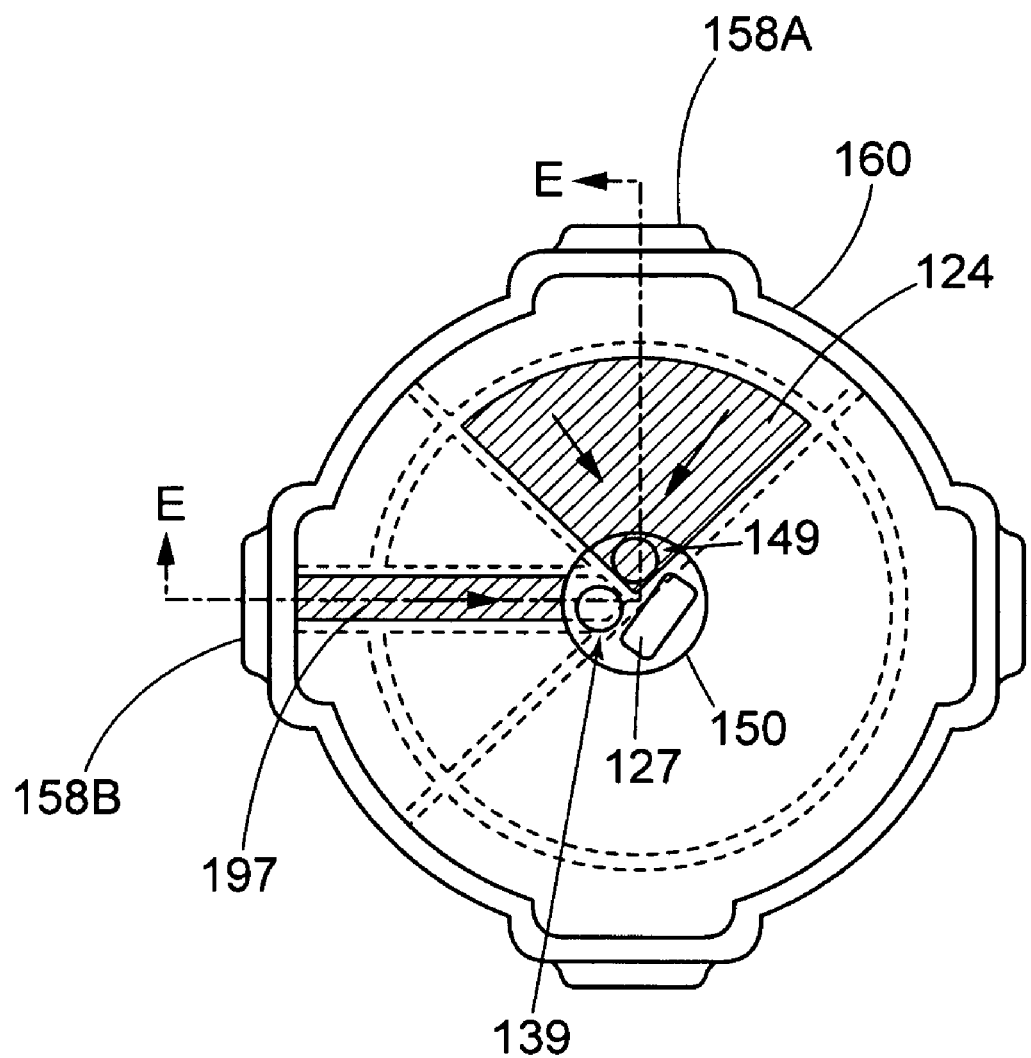
FIG. 12A is an elevational view of the proximal end of the filter cartridge assembly of FIG. 9A.
Figure 12B:
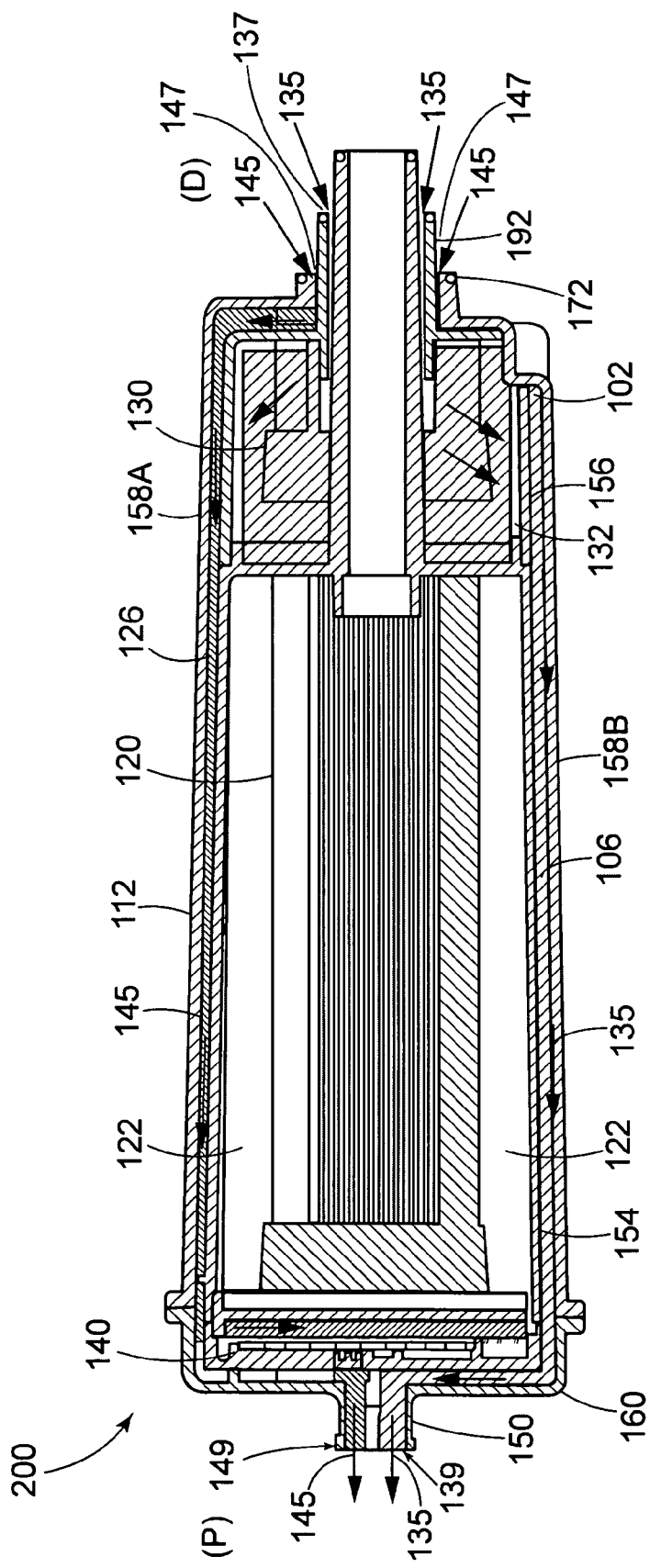
FIG. 12B is a cross-sectional view of the filter cartridge assembly of FIG. 9A taken along cut line E-E of FIG. 12A, which illustrates a second and a third flow path through the filter housing.

Disposed within the interior cavity of filter cartridge 200 are first, second and third filter elements, 120, 130 and 140, respectively. The first filter element 120 conditions fluid that traverses the first flow path 125 from a first inlet port 127 (referred to in FIG. 11 as the "suction connection slot") to a first outlet port 129. The second filter element 130 conditions fluid that traverses the second flow path 135 from a second inlet port 137 to a second outlet port 139 (referred to in FIG. 12B as the "pressure gas exit"). Lastly, the third filter element conditions fluid that traverses the third flow path 145 from a third inlet port 147 to a third outlet port 149 (referred to in FIG. 12B as the "insufflation gas exit"). As best shown in FIGS. 11, 12A and 12B, the first flow path 125 is isolated from the second and third flow paths, 135 and 145 respectively, and the second flow path 135 is isolated from the third flow path 145.

As shown in FIGS. 10 and 11, the first filter element 120 is a radially pleated filter. Fluid is conditioned in the first flow path 125 by traversing in a radially inward direction through the first filter element 120. As shown in FIGS. 10 and 12B, the second filter element 130 is also a radially pleated filter and fluid is conditioned in the second flow path 135 by traversing in a radially outward direction through the second filter element 130. Lastly, as shown in FIGS. 10 and 12B, the third filter element 140 is disc filter and fluid is conditioned in the second flow path 145 by traversing axially/proximally through the third filter element 140.

Referring now to FIG. 10, which provides an exploded perspective view of filter cartridge 200. As shown therein, housing 110 of the filter cartridge 200 includes an exterior body portion 112 and a proximal end cap 160. Unlike filter cartridge 100 which utilizes a double-walled housing 10 and a distal end cap 70, housing 110 for cartridge 200 has a single-walled exterior body portion 112 and first and second interior chamber segments, 154 and 156, respectively. The first and second interior chamber segments 154/156 of the housing 110 partially define the filter chambers for the first and second filter elements, 120/130.

The second interior chamber segment 156 includes a cylindrical neck portion 192 (FIG. 9A) which is inserted into the proximal end (P) of the exterior body portion 112 of the housing 110 until the neck portion 192 extends though the aperture formed in the distal end of the exterior body portion 112. The second filter element 130 is disposed within the second interior chamber segment and a second filter chamber 132 is established by inserting a cylindrical stem 189 associated with the first interior chamber segment 154 through the center of the second filter element 130 and into the bore of cylindrical neck portion 192. The first filter element 120 is contained within an interior cavity defined by the first interior chamber segment 154 and the first filter chamber 122 is established by sealing off the proximal end of the exterior body portion 112 using the disc holder 150 (see FIG. 10) and the proximal end cap 160. The third filter element 140 is supported in housing 112 by a disc holder 150, which includes an upper half 150a and a lower half 150b.

Figure 9C:
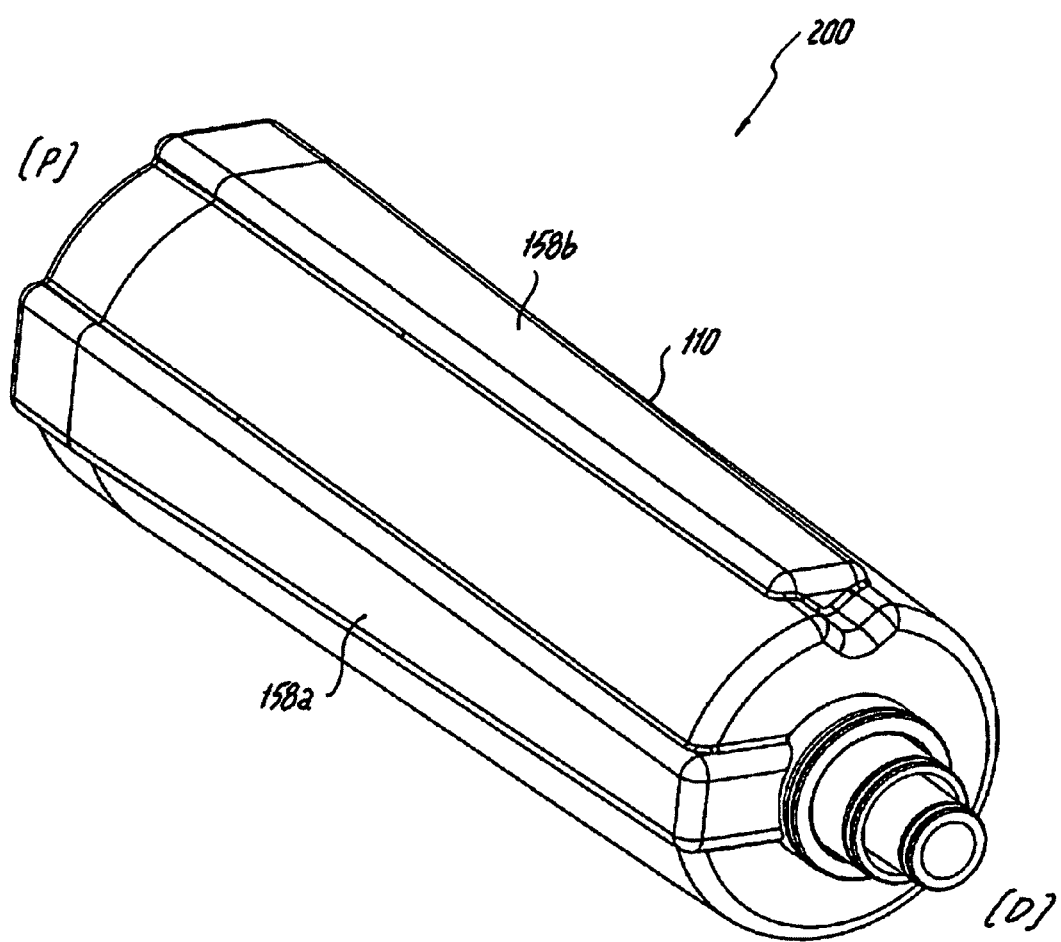
FIG. 9C provides a perspective view of the filter cartridge assembly of FIG. 9A.

As best shown in FIG. 9C, the exterior body portion of the housing 110 includes two longitudinal ribs 158a/158b that are spaced approximately 90 degrees apart. The ribs 158a/158b are used to create longitudinal channels or passageways between the inner wall of the exterior body portion 112 and the outer surfaces of the first and second interior chamber segments 154/156. As shown in this figure and to be discussed in detail hereinbelow, a portion of the second and third flow paths, 135 and 145, extend in the longitudinal channels defined between the interior chamber segments and the exterior body portion of the housing.

Referring now to FIGS. 9A, 9B 11, 12A and 12B, the proximal end (P) of the housing 110 includes a connector element 150. The connector element 150 houses the first inlet port 127 and the second and third outlet ports, 139 and 149, respectively. The connector element 150 also includes a male thread 152, similar to a luer lock fitting, which allows the filter cartridge 200 to be fluidly engaged with a tube set, for example, having a mating connector head. As best shown in FIGS. 9A, 11 and 12B, the first outlet port 129, the second inlet port 137 and third inlet port 147 are coaxially arranged at the distal end (D) of the housing 110.

As best shown in FIG. 11, the first flow path 125 extends from the first inlet port 127, a slotted hole formed in connector element 150 positioned, through a passage 104 (see FIG. 10) formed in the upper and lower disc holder halves 150a/150b and into the first filter chamber 122. Then fluid in the first flow path 125 is distributed around the circumference of the first filter element 120 and is conditioned by passing in a radially inward direction (see FIG. 11) through the filter media into the central core of the first filter element 120. The conditioned fluid then travels distally from the central core of the first filer element 120 into the bore defined in the cylindrical stem 189 of the first interior chamber segment 154 and exits the filter housing 110 through the first outlet port 129. (FIG. 11)

As best shown in FIGS. 12A and 12B, the second flow path 135 extends from the second inlet port 137 defined between the outer periphery of the cylindrical stem 189 of the first interior segment 154 and the cylindrical neck 192 of the second interior chamber segment 156 until it reaches the central core of the second filter element 130. Then the fluid in the second flow path 135 is conditioned by proceeding in a radially outward direction through the filter media of the second filter element 130 and the conditioned fluid is supplied through side aperture 102 (see FIG. 10) formed in the second interior chamber segment 156 to an axial flow passage 106 defined between rib 158b of the exterior body portion 112 and the outer peripheral walls of the first and second interior chamber segments 154/156. The conditioned fluid in axially flow passage 106 exits into a radially oriented channel 197 (see FIG. 12A) formed in the proximal end cap 160 and exits the proximal end (P) of the filter cartridge 200 through the second outlet port 139 formed in connector 150.

As best shown in FIGS. 12A and 12B, the third flow path 145 initially extends axially from the third inlet port 147, which is defined between the outer periphery of the cylindrical neck 192 of the second interior chamber segment 156 and the cylindrical neck 172 of exterior body portion 112 of housing 110, to a radially directed channel formed between rib 158a and the exterior surface of the second interior chamber segment 156. Fluid in the third flow path 145 is then supplied to a second axial flow passage 126 defined between rib 158a of the exterior body portion 112 and the outer peripheral walls of the first and second interior chamber segments 154/156. (FIG. 10) The fluid in the second axially flow passage 126 is directed through side aperture 172 (see FIG. 10) into the third filter chamber 142 defined by the upper and lower disc holder halves 150a/150b. Once in the third filter chamber 142 the fluid is conditioned by passing axially through the third filter element 140, a disc filter. The conditioned fluid is supplied to a wedge-shaped chamber 124 (see FIG. 12A) formed on the underside of the proximal end cap 160 and exits the housing 110 through the third outlet port 149 formed in connector 150.

Those skilled in the art will readily appreciate that the present invention is not limited to particular type of filter type or media, such as a radially pleated filter element. For example, a resin bonded cellulose type filter can be used or a fibrous media for filtering pathogenic microorganisms, such as bacteria, carbon block filter media, spiral wound media.

Referring now to FIGS. 13A-17, there is illustrated a filtration system which has been constructed in accordance with a preferred embodiment of the present invention and is designated generally by reference numeral 300. As will be described hereinbelow, filtration system 300 is adapted and configured for conditioning fluid received from three distinct fluid sources and for use in conjunction with the surgical trocar disclosed in U.S. patent application Ser. No. 11/960,701 and International Patent Application Publication No. WO 2008/077080, published on Jun. 26, 2008, which are herein incorporated by reference in their entireties.

Filtration system 300 includes, among other elements, a controller 310, a socket assembly 330 and the previously described filter cartridge assembly 100. As will be discussed in detail below, controller 310 includes mechanisms for regulating and monitoring fluid flow in filtration system 300.

The controller 310 has an outer housing 312 with planar upper and lower surfaces 314 and 316 respectively, and curved side walls 318a/318b. The side walls 318a/318b each include finger recesses 320a (opposite side, not shown)/320b for moving or manipulating the controller 310. The planar lower surface 316 allows the controller 310 to be placed on a utility cart or supported from the overhead of the operating room using a boom mechanism.

The front face 322 of controller 310 includes an analog gage 324, a dial 326, a power button 328 and a jack 329. The purpose and operation of these elements will be described hereinbelow. An elongated receptacle 340 or bore is formed in the housing 312 for the controller 310 and extends into the controller 310 from its front face 322. The receptacle 340 is adapted and configured for receiving the socket assembly 330 (see FIGS. 14-17). Those skilled in the art will readily appreciate that rather than an analog gage, a digital gage can be used and the controller can be equipped with additional dials, gages and readout devices.

Referring now to FIGS. 14-17, the socket assembly 330 functions as an adapter for releasably retaining the filter cartridge 100 in fluid communication with the controller 310. The socket assembly 330 includes a main body portion 332 which defines a central bore 334 into which the filter cartridge assembly 100 is inserted. A locking element 336 and a mounting ring 338 are positioned at the proximal end of the socket assembly 330. The mounting ring 338 has a plurality of holes formed in its periphery for fastening the socket assembly 330 to the controller 310.

The locking element 336 of the socket assembly 330 includes a cam mechanism which has a cam ring 342 with a lever arm 344 extending radially outward from its outer circumference. The lever arm 344 is used to rotate the cam ring 342 with respect to the main body portion 332 of the socket assembly 330. The cam ring 342 includes four axial slots 346 each of which terminates in pitched camming channels 348 (two shown in FIG. 14).

As shown in FIG. 2, the main body portion 12 of the housing 10 of filter cartridge assembly 100 has 4 radially-spaced apart cam lugs 62 and an alignment rib 64 formed on its outer periphery. Those skilled in the art will readily appreciate that the present invention is not limited to any particular number or orientation of cam lugs.

Figure 13A:
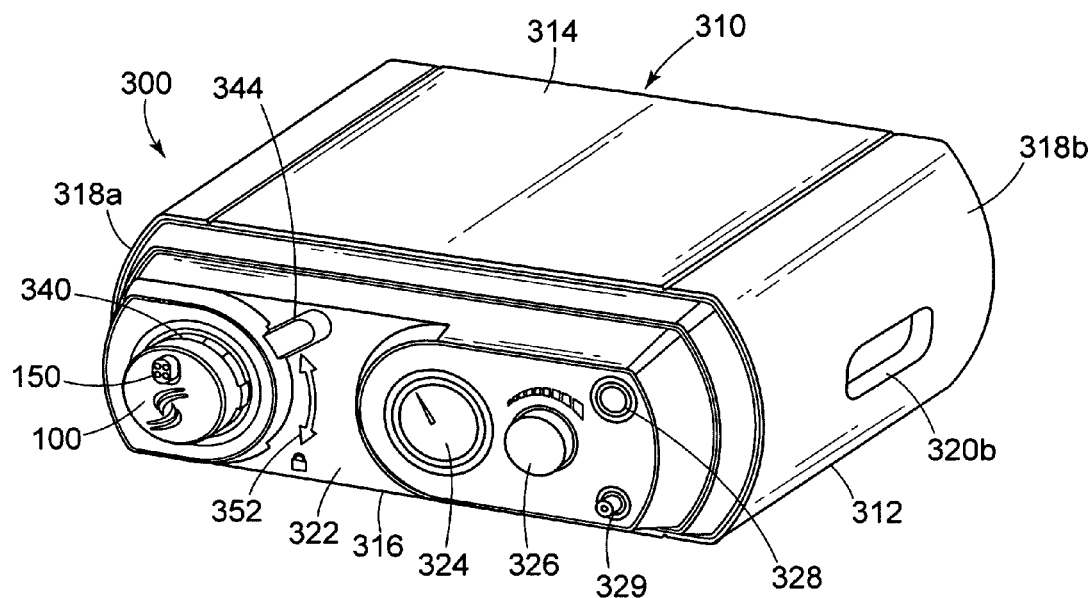
FIG. 13A is perspective view of a tri-flow filtration system which is constructed in accordance with an embodiment of the present invention and includes a controller/insufflator module and a filter cartridge assembly.
Figure 13B:
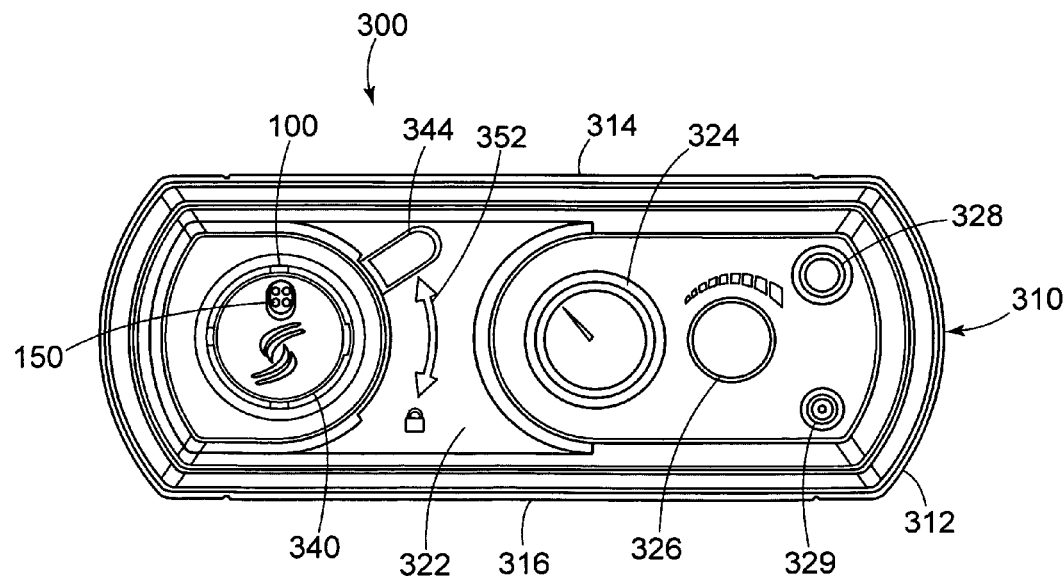
FIG. 13B is a front elevational view of the tri-flow filtration system of FIG. 13B.
Figure 14:
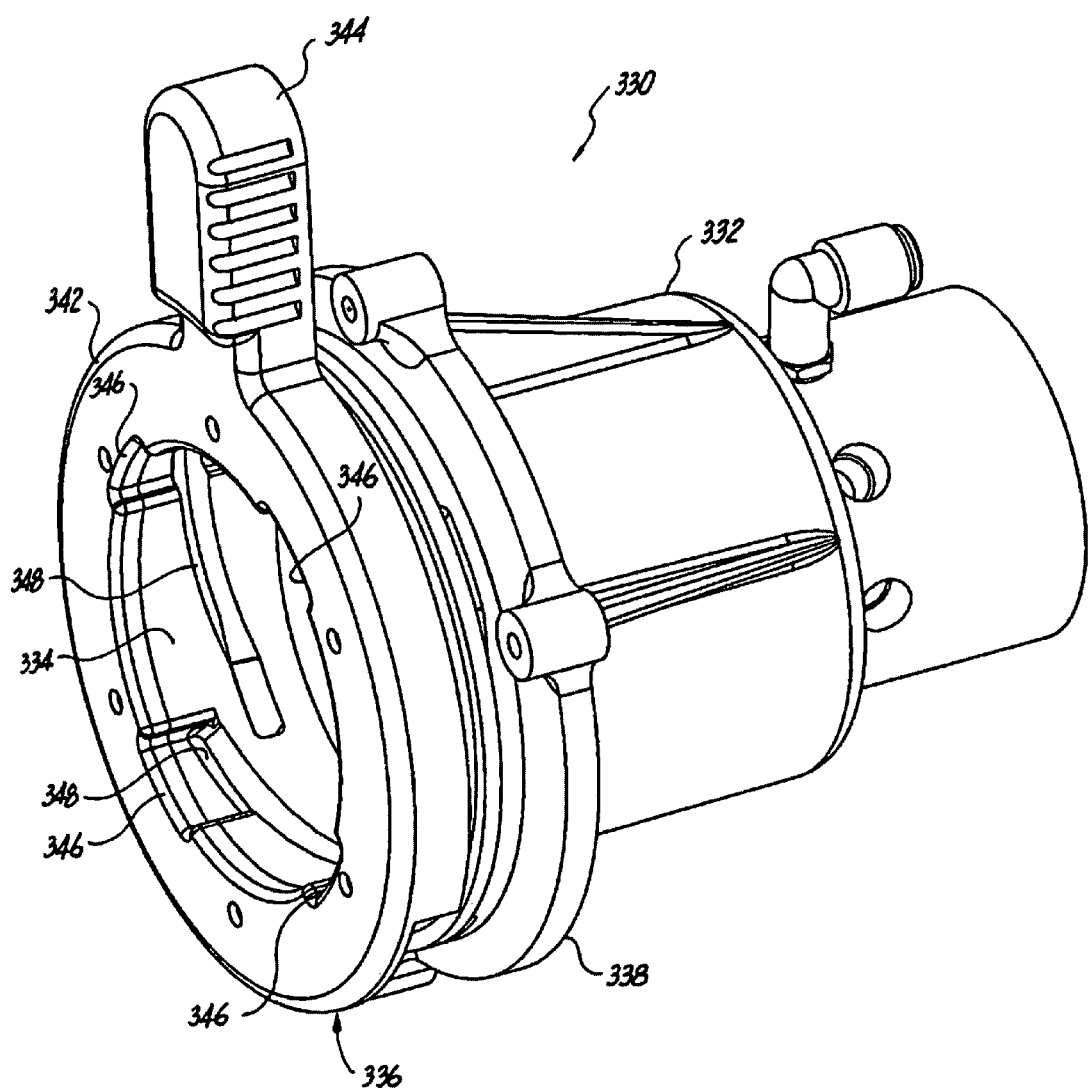
FIG. 14 is a perspective of view of a socket assembly which is adapted for use with the tri-flow filtration system of FIGS. 13A and 13B.
Figure 15:
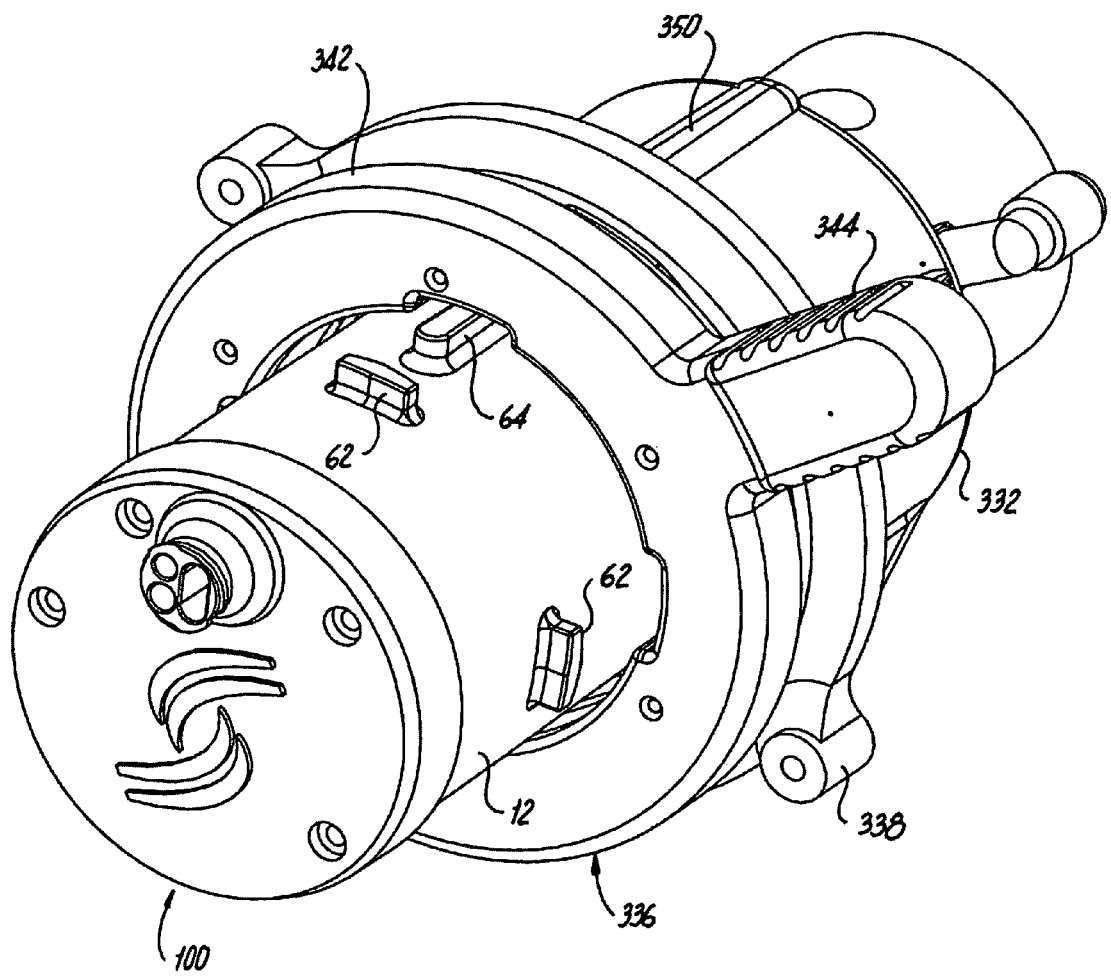
FIG. 15 is a perspective view of a filter cartridge assembly, which has been constructed in accordance with an embodiment of the present invention, partially inserted into the socket of FIG. 14.
Figure 16:
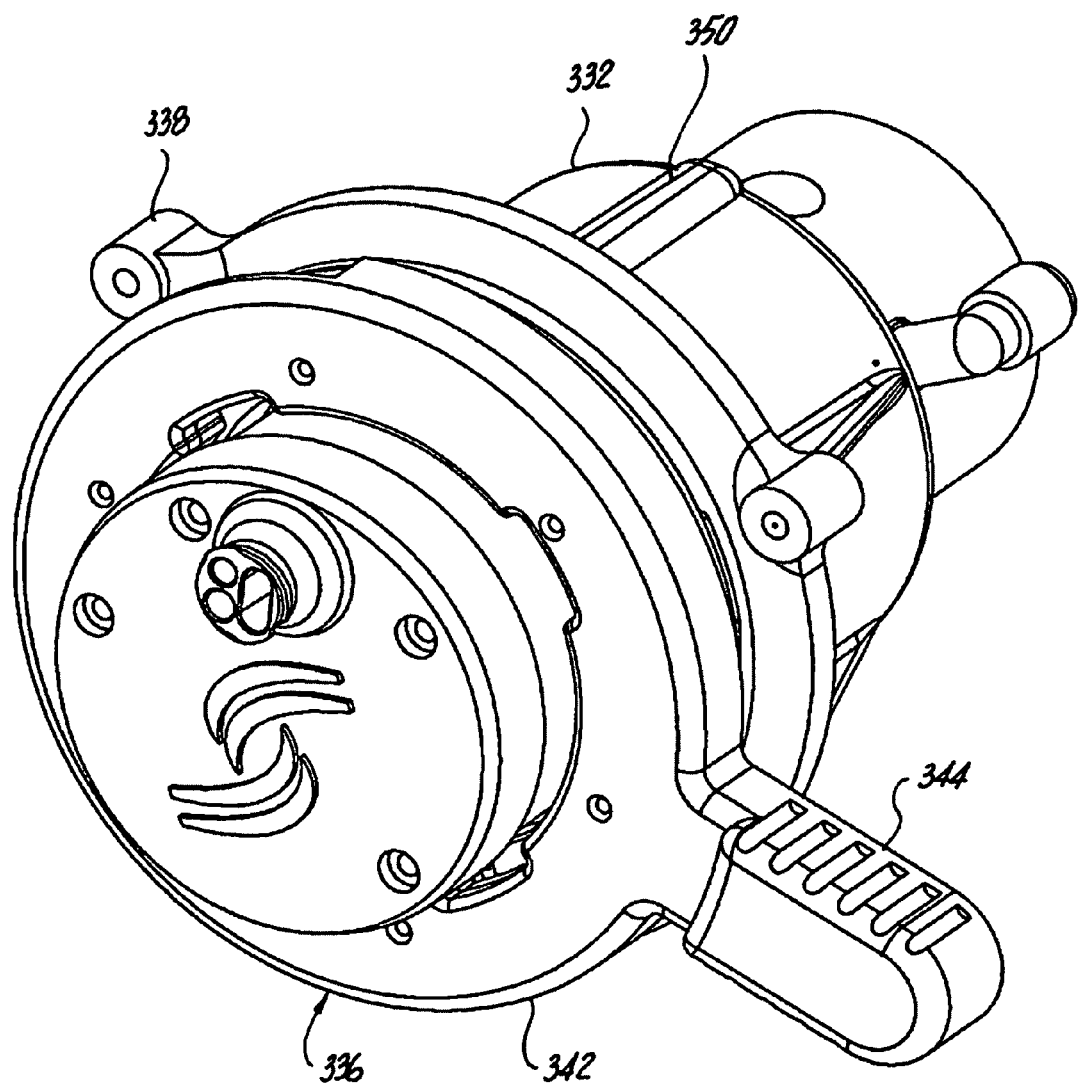
FIG. 16 is a perspective view of a filter cartridge assembly, which has been constructed in accordance with an embodiment of the present invention, fully inserted into the socket assembly of FIG. 14.
Figure 17:
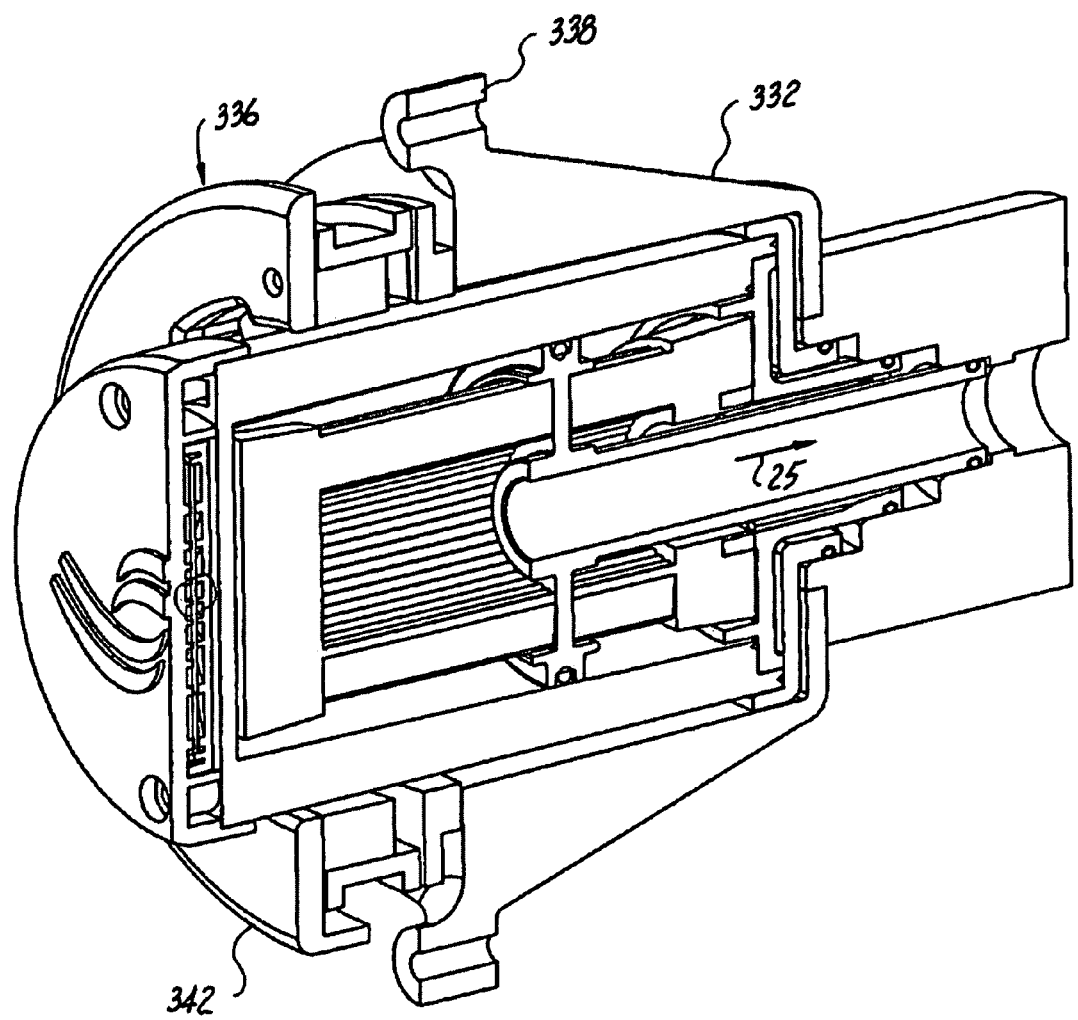
FIG. 17 is a cross-sectional view of a filter cartridge assembly fully inserted into the socket assembly of FIG. 14.

As shown in FIG. 15, when filter cartridge assembly 100 is inserted into the central bore 334 of the socket assembly 330 each alignment rib 64 must be oriented such that it can be received into a respective mating channel 350 (identified from the exterior) formed in the main body portion 332 of the socket assembly 330 (see FIG. 15). Moreover, the camming lugs 62 must each pass through the axial slots 346 of the cam ring 342 and into respective pitched camming channels 348. When the cam ring 342 is rotated with respect to the filter cartridge assembly 100, by rotating lever arm 344 as shown in FIGS. 13A and 13B (see directional arrow 352), the camming lugs 62 formed on the outer periphery of housing 12 are trapped in the pitched camming channels 348 and the filter cartridge assembly 100 is forced further into the central bore 334 of the socket assembly 330 and secured in fluid communication with the controller 310. (See FIGS. 16 and 17).

Figure 18:
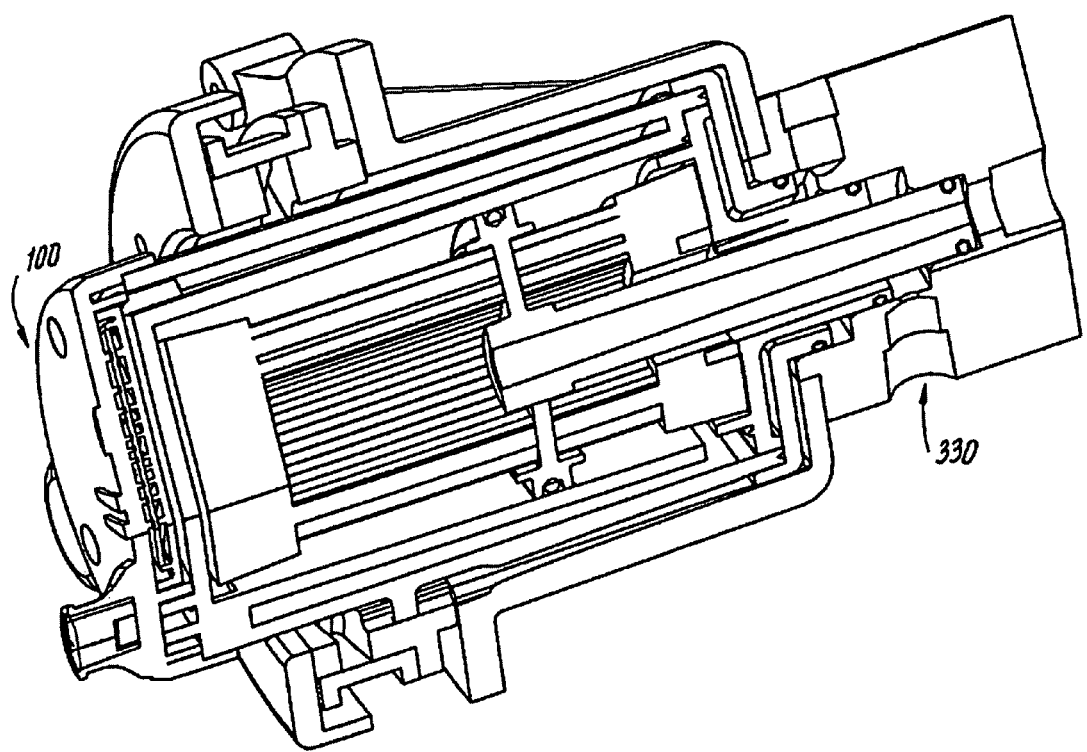
FIG. 18 is a cross-sectional view of a filter cartridge assembly fully inserted into the socket assembly of FIG. 14, which illustrates the fluid communication between the socket assembly and the filter cartridge assembly.

As shown in FIG. 18, fluid in the first flow path exits the filter assembly 100 along the central axis and passes through an axial port formed in socket assembly 330. Fluid is supplied to the second and third flow paths in the filter assembly through radially directed ports formed in the socket assembly 330.

In operation controller 310 can include an insufflation unit and be connected to surgical trocar, similar to that disclosed in U.S. patent application Ser. No. 11/960,701 and International Patent Application Publication No. WO 2008/077080, published on Jun. 26, 2008. The trocar can be connected to the controller 310 by way of fluid conduits or a tube set (not shown). In the embodiment disclosed herein, the controller does not include an insufflator but receives insufflation gas from an insufflator through jack 329. The insufflator would receive the gas from, for example, a supply tank and a pressure regulator would normally be provided between the tank and the insufflator.

The operation of the controller is described in detail in U.S. patent application Ser. No. 11/960,701 and International Patent Application Publication No. WO 2008/077080, published on Jun. 26, 2008, and will not be repeated herein. As noted in these references, the system for surgical insufflation and recirculation disclosed therein requires the filtering of three separate fluid sources. The controller 310 can be utilized with any embodiments of the systems described these application. As illustrated in FIGS. 13A and 13B, controller 310 includes a settable dial 326 for setting the desired pressure output from the controller, and a pressure gauge 324 for confirming the set pressure.

As illustrated, the filter cartridge assembly 100 mounts directly to the control unit 310, such that a low profile is presented. In such a configuration, the first flow path 25 of the filter cartridge assembly 100 would be used to filter gas being removed from the abdomen patient (suction line) or for the removal of spent insufflation fluid. The second flow path 35 of filter cartridge assembly 100 would be used for conditioning the pressured gas being provided to the trocar for use in sealing the lumen used to pass instruments and the like through the trocar. The third flow path 45 of filter cartridge assembly 100 would be used to condition the pressurized gas used for insufflation and sensing.

FIGS. 19-27 illustrate a filter cartridge assembly 1900 constructed in accordance with a further aspect of the present invention. As with foregoing embodiments, the filter cartridge assembly includes a plurality of filter elements for filtering a plurality of fluid flow paths. Differences are provided in the shape of the housing 1920, flow paths formed therewithin, and other features. However, with the filter 1900, features similar to those of the filter cartridge 100 are illustrated and not necessarily described explicitly.

Figure 19:
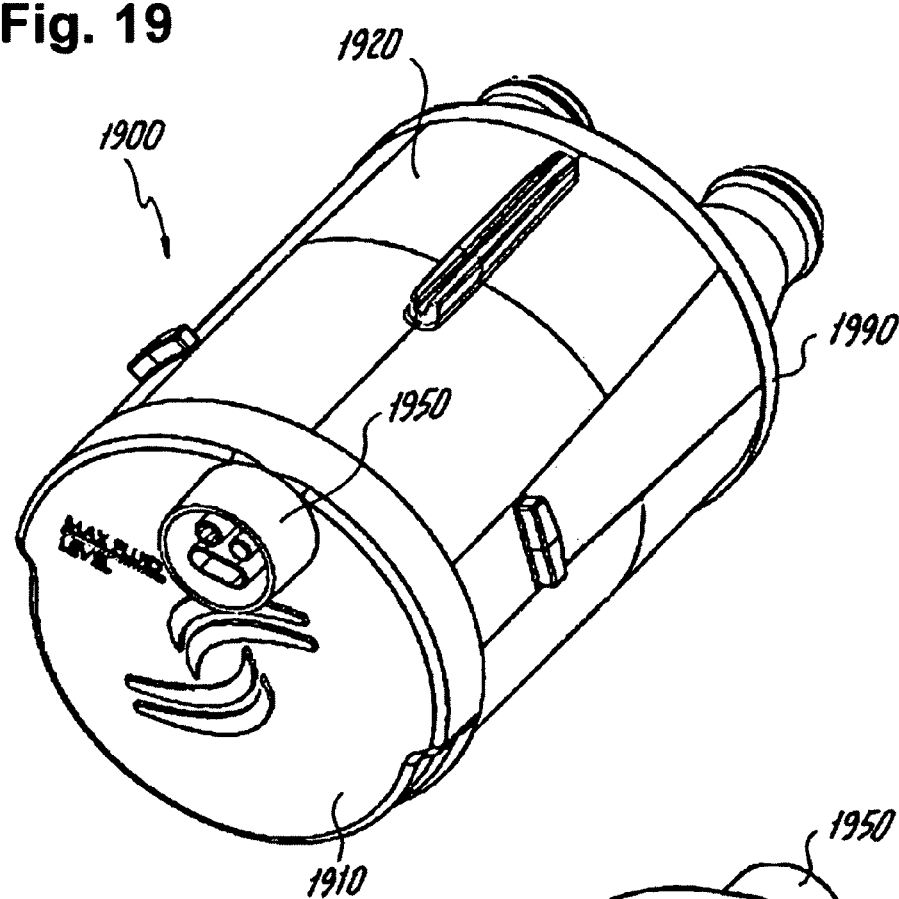
FIG. 19 is a front-top isometric view of a filter cartridge assembly constructed in accordance with a further aspect of the present invention.
Figure 20:
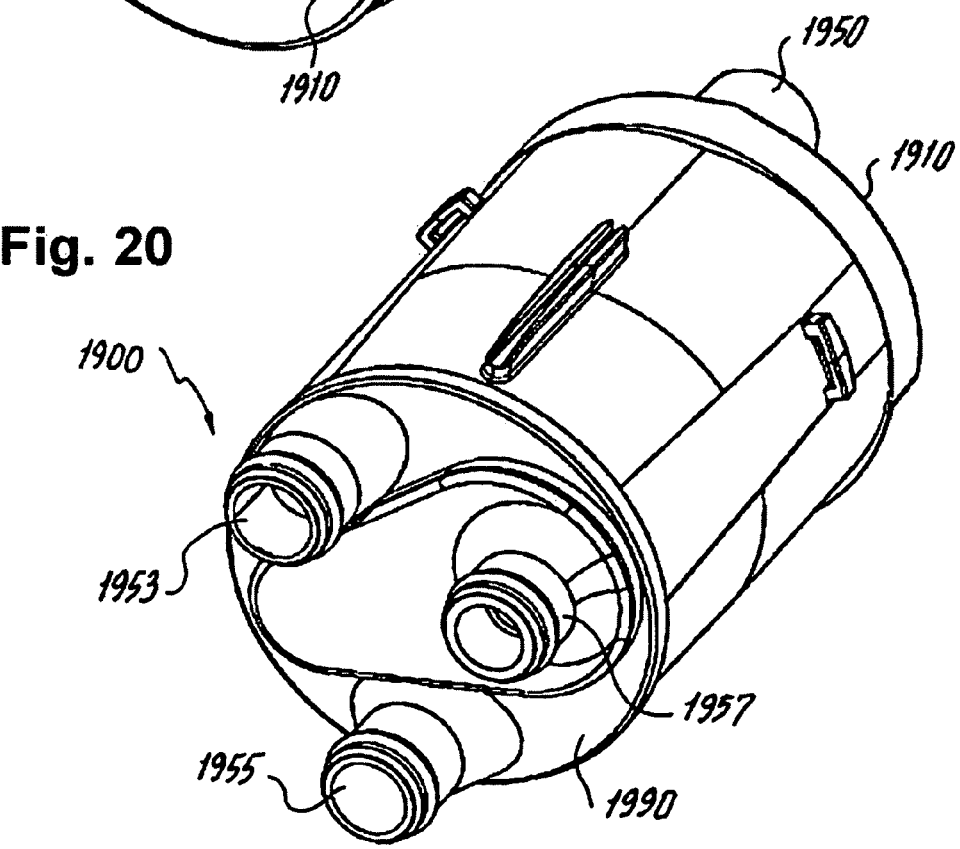
FIG. 20 is a rear-top isometric view of the filter cartridge assembly of FIG. 19.

As best seen in FIGS. 19 and 20, the filter cartridge 1900 includes a connection 1950 for a tube set, a front end cap 1910, housing 1920 and rear end cap 1990. In the rear end cap 1990 are defined ports for connection with a recirculation unit. One port 1953 is for supply pressure from the unit, through the filter cartridge 1900, one port 1957 is for insufflation and pressure sensing through the cartridge 1900, and one port 1955 is for return from the cartridge into the unit.

Figure 26:
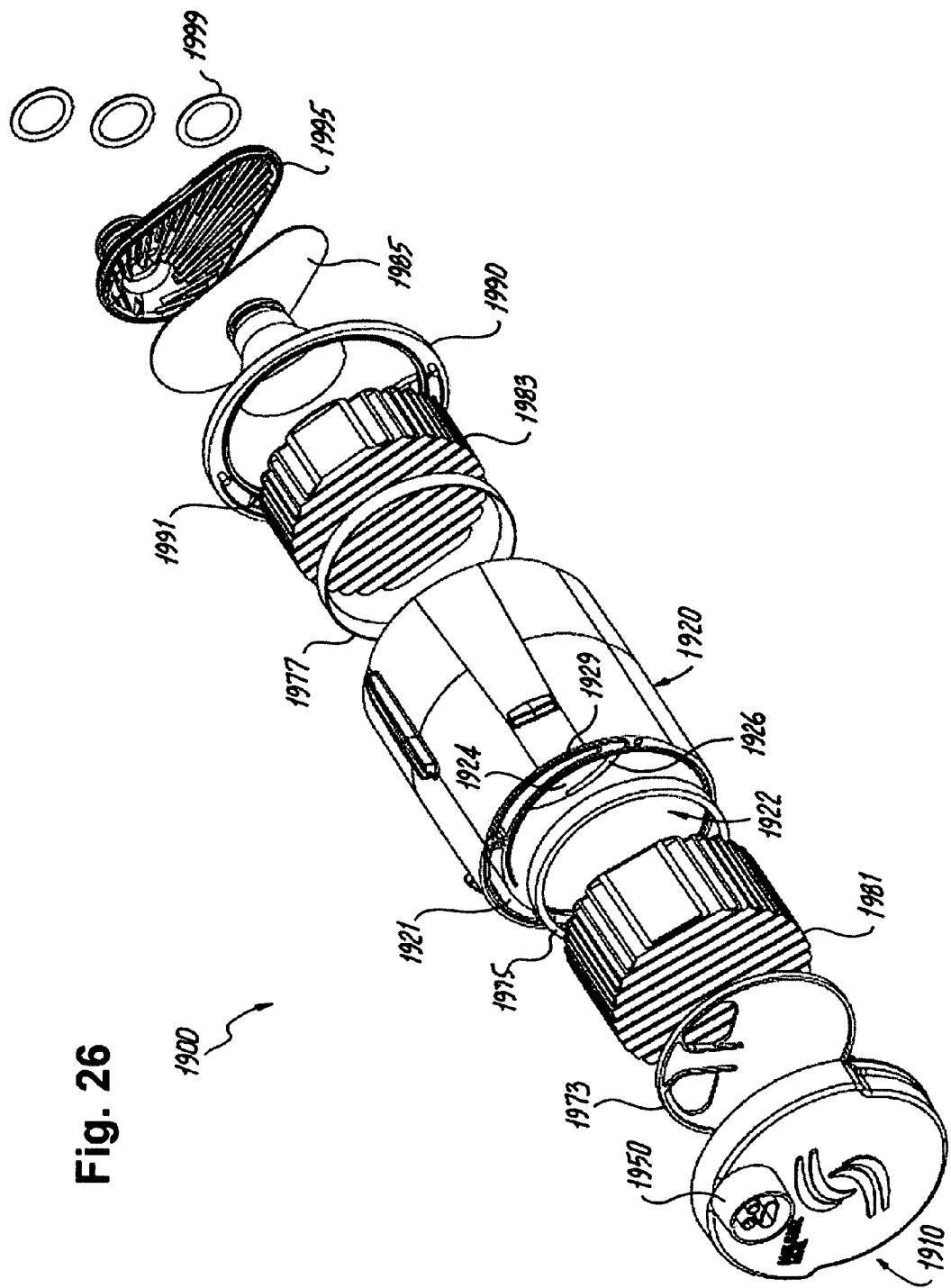
FIG. 26 is a front-top exploded isometric view of the filter cartridge assembly of FIG. 19.
Figure 27:
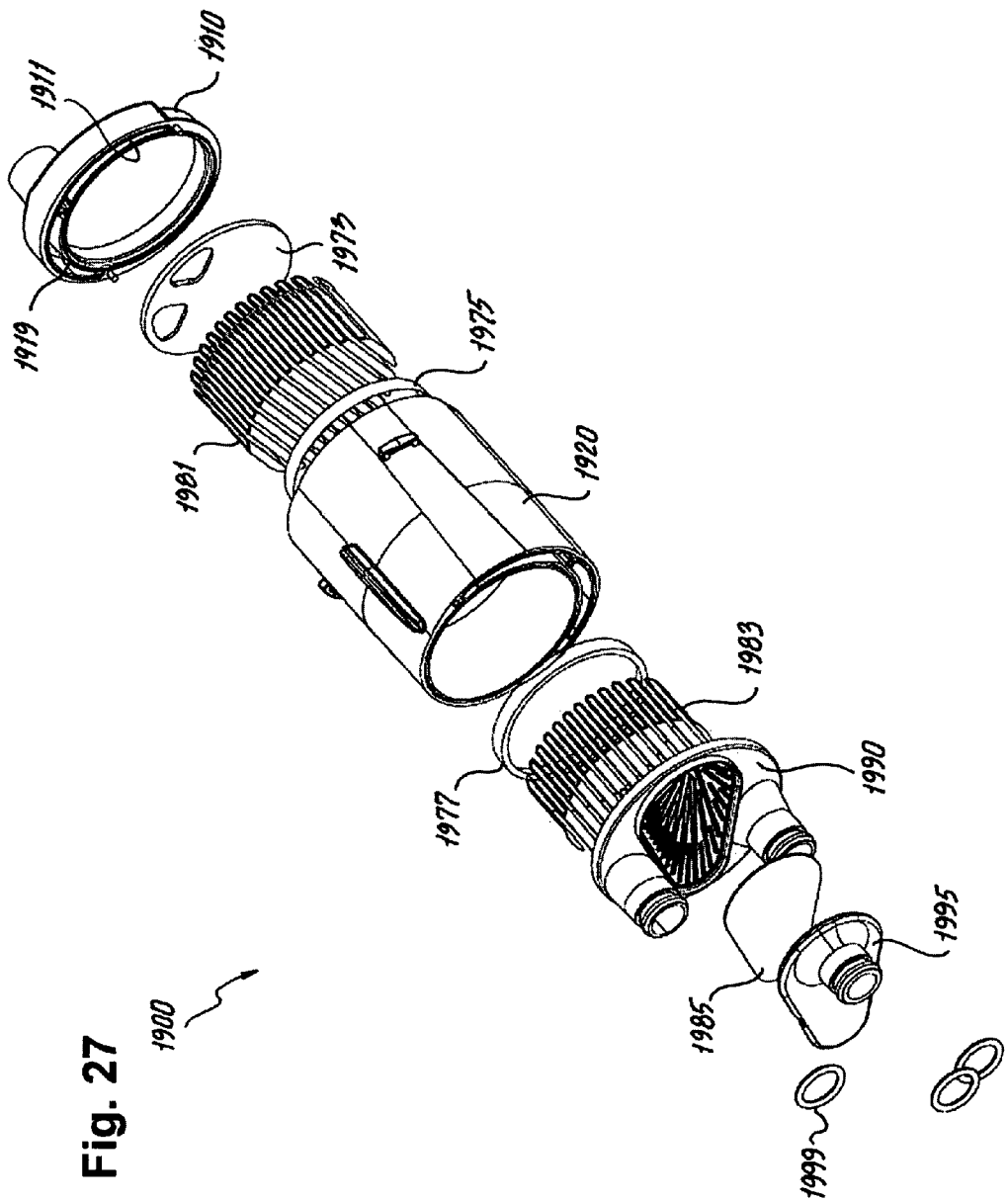
FIG. 27 is a rear-top exploded isometric view of the filter cartridge assembly of FIG. 19.

In the exploded views of FIGS. 26 and 27, the parts that can be seen, and the function thereof, are as follows. The front end cap 1910 distributes flow from the connection 1950 thereon. Recirculation flow goes from a tube set, through the lower wide port of the connector 1950, and into a chamber defined between the front plate 1910 and a separating plate 1973, which helps hold fluid and prevent it from reaching the recirculation filter 1981, which is a horizontal pleated filter, shaped as a cylinder. The filter 1981 is held off the bottom of its chamber 1922 in the housing 1920 by a tapered ring, which has a substantially triangular cross-section, the small end of which abuts a central wall 1924 in the housing 1920. Return flow passes through the filter 1981 and through a channel 1926 in the housing, through another passage in the rear end plate 1990, and to the respective port 1955.

Insufflation pressure passes from its port 1957, into a chamber defined by rear housing portion 1995 in the rear end plate 1990, through a flat filter 1985, into a channel 1921 defined in the housing 1920, into a channel 1911 formed in the front end cap, and through a respective port on the connector 1950.

Pressure from the unit flows through its designated port 1953, into a rear chamber defined for the pressure filter 1983 by the housing 1920 and the end plate 1990. A ring 1977 is also provided to hold the filter off of the dividing wall 1924. A channel 1929 then carries the pressure through the housing 1920, into the front end cap 1910, where a channel 1919 directs the flow through the connector 1950.

The filters 1983 and 1981 are preferably sealed against the housing 1920 by an adhesive. Grooves and matching ridges can be provided between adjoining housing sections, such can be adhered by an adhesive or by other suitable means, such as ultrasonic welding. In accordance with the invention, the filter 1900 can be configured such that channels formed in the wall of the housing 1920, such as channels 1921, 1929, and an offset arrangement of the pleated filter elements 1981, 1983 result in a housing cross-section that is not circular but has lobular portions in cross-section, corresponding to such channels.

Figure 28:
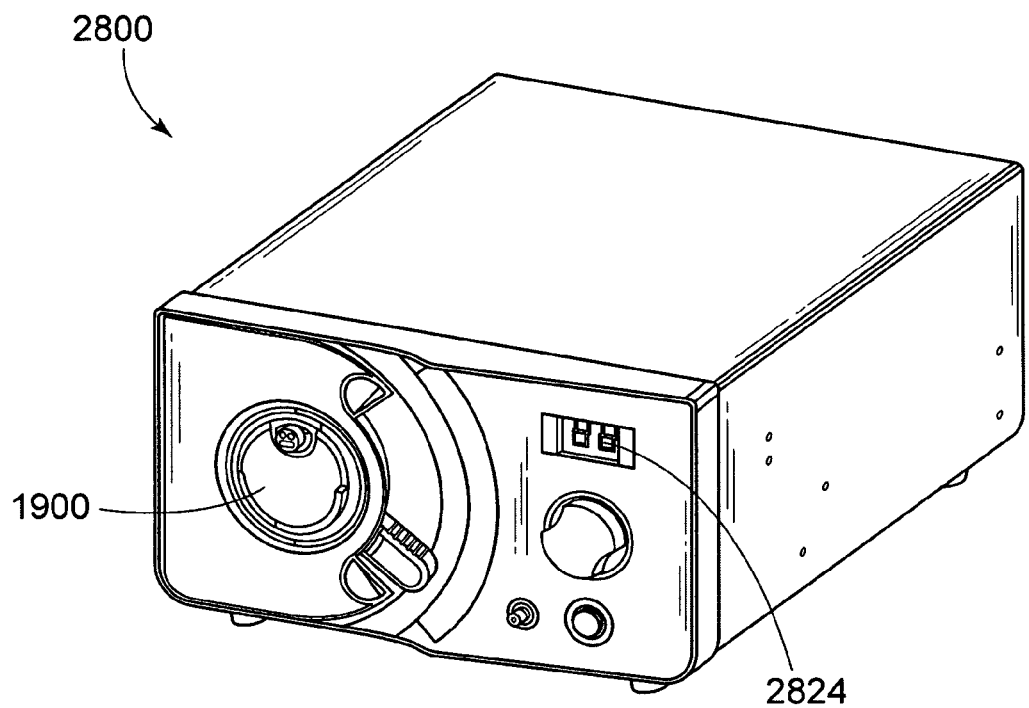
FIG. 28 is perspective view of a further embodiment of a tri-flow filtration system which is constructed in accordance with an embodiment of the present invention and includes a controller/insufflator module and a filter cartridge assembly.
Figure 29:
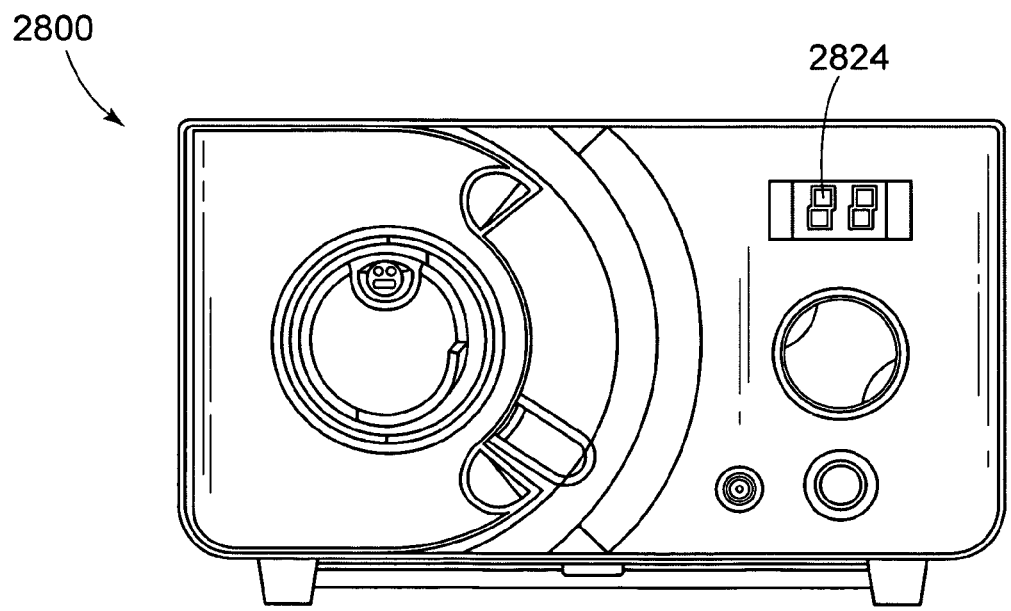
FIG. 29 is a front elevational view of the tri-flow filtration system of FIG. 28.

FIG. 28-29 illustrate a further embodiment of a tri-flow filtration system 2800 which is constructed in accordance with an embodiment of the present invention and includes a controller/insufflator module and a filter cartridge assembly 1900. The system 2800 includes a digital readout 2824, but otherwise includes features similar to the embodiment of FIGS. 13A and 13B.

Figure 30:
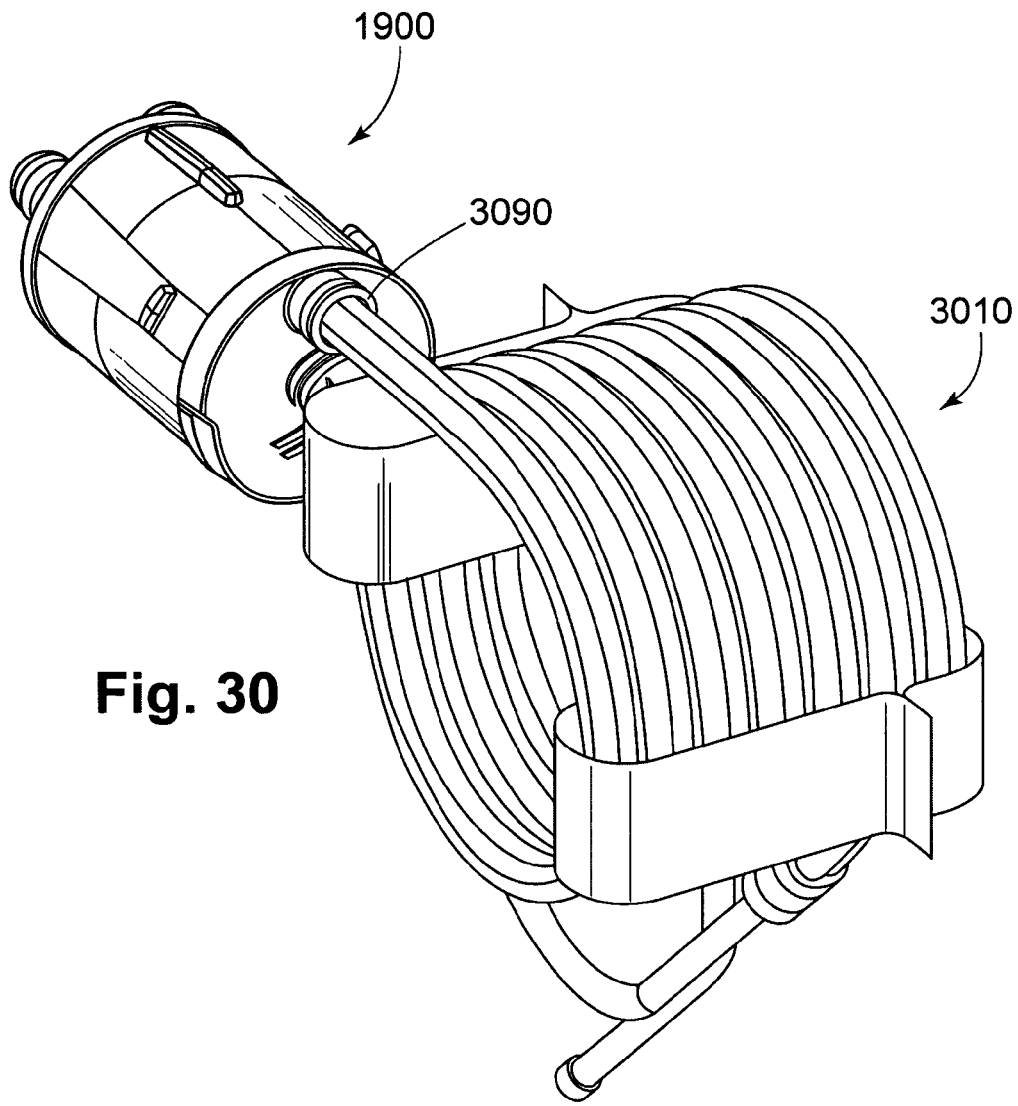
FIG. 30 is a front-top isometric view of a filter cartridge assembly of FIG. 19 with an integral tube set therefor.
Figure 31:
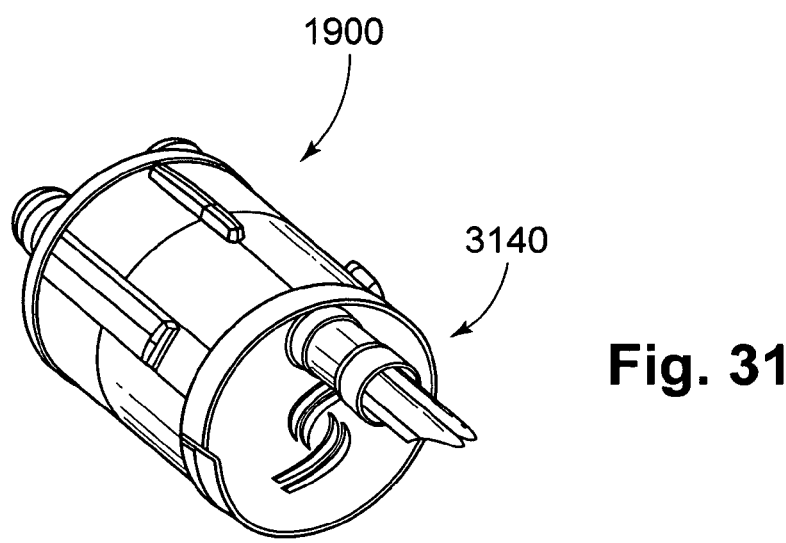
FIG. 31 is a front-top isometric view of a filter cartridge assembly of FIG. 19 adapted with a connector for use with a separable tube set.
Figure 32:
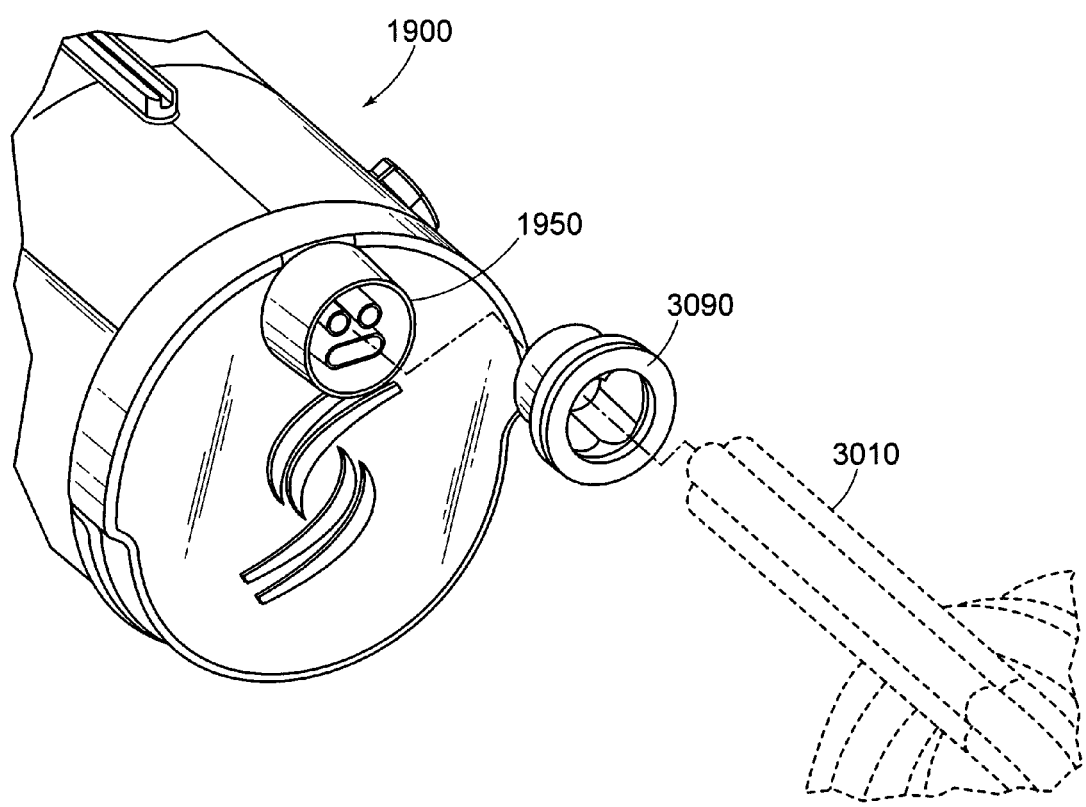
FIG. 32 is an isometric detail view of a filter cartridge assembly of FIG. 19 adapted with a connector for use with a separable tube set, illustrating a connecting bushing therefor.
Figure 33:
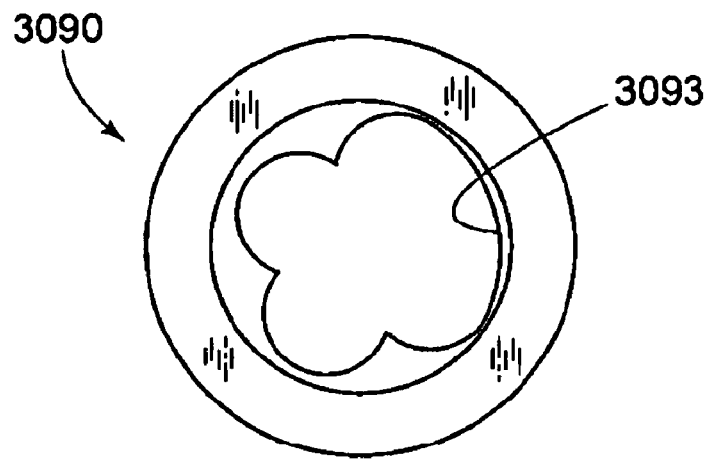
FIG. 33 is a front elevational view of the bushing of FIG. 32.
Figure 34:
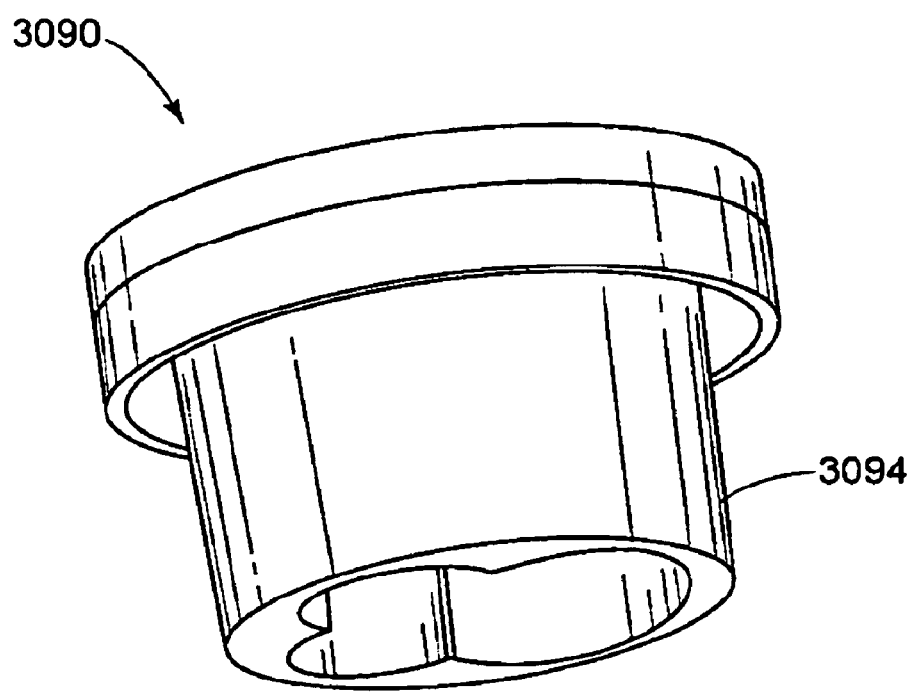
FIG. 34 is a bottom isometric view of the bushing of FIG. 32.

FIG. 30 is a front-top isometric view of a filter cartridge assembly of FIG. 19 with an integral tube set 3010 therefor. A bushing 3090 is provided for connecting the tri-lumen tube of the tube set 3010 to the filter housing 1900. A detachable connection 3140 can alternatively be provided. The bushing 3090, as illustrated in FIGS. 33 and 34, includes an interior contour 3093 matching the tube substantially, and an outer taper 3094 for interfacing with the connection 1950, and facilitating a compression fitting of the tube set 3010 and the filter 1900. Adhesive can be used to facilitate a seal therebetween.

What is claimed is:

1. A filter cartridge assembly comprising:
   i) an elongated housing having axially opposed proximal and distal ends, the housing defining an interior cavity, a central axis and first, second and third flow paths which extend from the proximal end of the housing to the distal end, wherein the housing includes a pair of coaxially positioned peripheral walls;
   ii) a first filter element disposed along the central axis and within the interior cavity of the housing for conditioning fluid traversing the first flow path from a first inlet port to a first outlet port;
   iii) a second filter element disposed along the central axis and within the interior cavity of the housing for conditioning fluid traversing the second flow path from a second inlet port to a second outlet port; and
   iv) a third filter element disposed along the central axis and within the interior cavity of the housing for conditioning fluid traversing the third flow path from a third inlet port to a third outlet port; and wherein the first flow path is isolated from the second and third flow paths and the second flow path is isolated from the third flow path.

2. A filter cartridge assembly as recited in claim 1, wherein a portion of each of the second and third flow paths traverse axially between the peripheral walls of the housing.

3. A filter cartridge assembly as recited in claim 1, wherein the first filter element is radially pleated filter and fluid is conditioned in the first flow path by traversing in a radially inward direction through the first filter element.

4. A filter cartridge assembly as recited in claim 1, wherein the second filter element is radially pleated filter and fluid is conditioned in the second flow path by traversing in a radially outward direction through the second filter element.

5. A filter cartridge assembly as recited in claim 1, wherein the third filter element is a disc filter and fluid is conditioned in the second flow path by traversing axially through the third filter element.

6. A filter cartridge assembly as recited in claim 1, wherein the housing includes a cylindrical inner housing element positioned within the interior cavity of the housing and forming a first chamber for the first filter element.

7. A filter cartridge assembly as recited in claim 1, wherein the proximal end of the housing includes a connector element.

8. A filter cartridge assembly as recited in claim 7, wherein the connector element includes the first inlet port and the second and third outlet ports.

9. A filter cartridge assembly as recited in claim 1, wherein the housing includes two longitudinal ribs which define two longitudinal channels in the interior cavity of the housing and the second flow path traverse one of the channels and the third flow path traverses the other channel.

10. A filter cartridge assembly as recited in claim 6, wherein the housing further includes a second inner housing element positioned within the interior cavity of the housing and forming a second chamber for the second filter element.

11. A filter cartridge assembly as recited in claim 1, wherein the first outlet port, the second inlet port and third inlet port are located at the distal end of the housing.

12. A filter cartridge assembly as recited in claim 11, wherein the first outlet port, the second inlet port and the third inlet port are coaxially arranged.

13. A filtration system for conditioning fluid received from three distinct fluid sources, comprising:
   i) a controller including means for regulating and monitoring fluid flow in the filtration system, the controller defining an elongated receptacle;
   ii) a socket assembly positioned at least partially within the elongated receptacle defined by the controller, the socket assembly including a locking element; and
   iii) a filter cartridge assembly inserted into the socket assembly and secured in fluid communication with the controller by the locking element.

14. A filtration system as recited in claim 13, wherein the locking element includes a cam mechanism for engaging a lug extending from an exterior surface of the filter cartridge assembly.

15. A filtration system as recited in claim 13, wherein the filter cartridge assembly includes:
   i) an elongated housing having axially opposed proximal and distal ends, the housing defining an interior cavity and first, second and third flow paths which extend from the proximal end of the housing to the distal end;
   ii) a first filter element disposed within the interior cavity of the housing for conditioning fluid traversing the first flow path from a first inlet port to a first outlet port;
   iii) a second filter element disposed within the interior cavity of the housing for conditioning fluid traversing the second flow path from a second inlet port to a second outlet port; and
   iv) a third filter element disposed within the interior cavity of the housing for conditioning fluid traversing the third flow path from a third inlet port to a third outlet port; and wherein the first flow path is isolated from the second and third flow paths and the second flow path is isolated from the third flow path.

16. The system of claim 15, wherein the proximal end of the filter cartridge assembly housing includes a connector element.

17. The system of claim 16, wherein the connector element includes the first inlet port and the second and third outlet ports.

18. The system of claim 15, wherein the housing of the filter cartridge assembly includes a pair of coaxially positioned peripheral walls.

19. The system of claim 18, wherein a portion of each of the second and third flow paths traverse axially between the peripheral walls of the housing of the filter cartridge assembly.

20. The system of claim 15, wherein the first filter element is radially pleated filter and fluid is conditioned in the first flow path by traversing in a radially inward direction through the first filter element.

21. The system of claim 15, wherein the second filter element is radially pleated filter and fluid is conditioned in the second flow path by traversing in a radially outward direction through the second filter element.

22. The system of claim 15, wherein the third filter element is a disc filter and fluid is conditioned in the second flow path by traversing axially through the third filter element.

23. The system of claim 15, wherein the housing of the filter cartridge assembly further includes a second inner housing element positioned within the interior cavity of the housing and forming a second chamber for the second filter element.

24. The system of claim 15, wherein the housing of the filter cartridge assembly includes two longitudinal ribs which define two longitudinal channels in the interior cavity of the housing and the second flow path traverse one of the channels and the third flow path traverses the other channel.

25. The system of claim 15, wherein the first outlet port, the second inlet port and third inlet port are located at the distal end of the housing of the filter cartridge assembly.

26. The system of claim 25, wherein the first outlet port, the second inlet port and the third inlet port are coaxially arranged.

27. A filter cartridge assembly comprising:
 i) an elongated housing having axially opposed proximal and distal ends, the housing defining an interior cavity, a central axis and first, second and third flow paths which extend from the proximal end of the housing to the distal end;
 ii) a first filter element disposed along the central axis and within the interior cavity of the housing for conditioning fluid traversing the first flow path from a first inlet port to a first outlet port;
 iii) a second filter element disposed along the central axis and within the interior cavity of the housing for conditioning fluid traversing the second flow path from a second inlet port to a second outlet port; and
 iv) a third filter element disposed along the central axis and within the interior cavity of the housing for conditioning fluid traversing the third flow path from a third inlet port to a third outlet port, wherein:
  (a) the first flow path is isolated from the second and third flow paths;
  (b) the second flow path is isolated from the third flow path;
  (c) the third filter element is a disc filter; and
  (d) fluid is conditioned in the second flow path by traversing axially through the third filter element.

28. A filter cartridge assembly as recited in claim 27, wherein the proximal end of the housing includes a connector element.

29. A filter cartridge assembly as recited in claim 28, wherein the connector element includes the first inlet port and the second and third outlet ports.

30. A filter cartridge assembly as recited in claim 27, wherein the housing includes a pair of coaxially positioned peripheral walls.

31. A filter cartridge assembly as recited in claim 30, wherein a portion of each of the second and third flow paths traverse axially between the peripheral walls of the housing.

32. A filter cartridge assembly as recited in claim 27, wherein the first filter element is radially pleated filter and fluid is conditioned in the first flow path by traversing in a radially inward direction through the first filter element.

33. A filter cartridge assembly as recited in claim 27, wherein the second filter element is radially pleated filter and fluid is conditioned in the second flow path by traversing in a radially outward direction through the second filter element.

34. A filter cartridge assembly as recited in claim 27, wherein the housing includes a cylindrical inner housing element positioned within the interior cavity of the housing and forming a first chamber for the first filter element.

35. A filter cartridge assembly as recited in claim 34, wherein the housing further includes a second inner housing element positioned within the interior cavity of the housing and forming a second chamber for the second filter element.

36. A filter cartridge assembly as recited in claim 27, wherein the housing includes two longitudinal ribs which define two longitudinal channels in the interior cavity of the housing and the second flow path traverse one of the channels and the third flow path traverses the other channel.

37. A filter cartridge assembly as recited in claim 27, wherein the first outlet port, the second inlet port and third inlet port are located at the distal end of the housing.

38. A filter cartridge assembly as recited in claim 37, wherein the first outlet port, the second inlet port and the third inlet port are coaxially arranged.

39. A filter cartridge assembly comprising:
 i) an elongated housing having axially opposed proximal and distal ends, the housing defining an interior cavity, a central axis and first, second and third flow paths which extend from the proximal end of the housing to the distal end, wherein the housing includes a cylindrical inner housing element positioned within the interior cavity of the housing and forming a first chamber for the first filter element
 ii) a first filter element disposed along the central axis and within the interior cavity of the housing for conditioning fluid traversing the first flow path from a first inlet port to a first outlet port;
 iii) a second filter element disposed along the central axis and within the interior cavity of the housing for conditioning fluid traversing the second flow path from a second inlet port to a second outlet port; and
 iv) a third filter element disposed along the central axis and within the interior cavity of the housing for conditioning fluid traversing the third flow path from a third inlet port to a third outlet port; and wherein the first flow path is isolated from the second and third flow paths and the second flow path is isolated from the third flow path.

40. A filter cartridge assembly as recited in claim 39, wherein the proximal end of the housing includes a connector element.

41. A filter cartridge assembly as recited in claim 40, wherein the connector element includes the first inlet port and the second and third outlet ports.

42. A filter cartridge assembly as recited in claim 39, wherein the housing includes a pair of coaxially positioned peripheral walls.

43. A filter cartridge assembly as recited in claim 42, wherein a portion of each of the second and third flow paths traverse axially between the peripheral walls of the housing.

44. A filter cartridge assembly as recited in claim 39, wherein the first filter element is radially pleated filter and fluid is conditioned in the first flow path by traversing in a radially inward direction through the first filter element.

45. A filter cartridge assembly as recited in claim 39, wherein the second filter element is radially pleated filter and fluid is conditioned in the second flow path by traversing in a radially outward direction through the second filter element.

46. A filter cartridge assembly as recited in claim 39, wherein the third filter element is a disc filter and fluid is conditioned in the second flow path by traversing axially through the third filter element.

47. A filter cartridge assembly as recited in claim 39, wherein the housing further includes a second inner housing element positioned within the interior cavity of the housing and forming a second chamber for the second filter element.

48. A filter cartridge assembly as recited in claim 11, wherein the housing includes two longitudinal ribs which define two longitudinal channels in the interior cavity of the housing and the second flow path traverse one of the channels and the third flow path traverses the other channel.

49. A filter cartridge assembly as recited in claim 11, wherein the first outlet port, the second inlet port and third inlet port are located at the distal end of the housing.

50. A filter cartridge assembly as recited in claim 49, wherein the first outlet port, the second inlet port and the third inlet port are coaxially arranged.

51. A filter cartridge assembly comprising:
   i) an elongated housing having axially opposed proximal and distal ends, the housing defining an interior cavity, a central axis and first, second and third flow paths which extend from the proximal end of the housing to the distal end;
   ii) a first filter element disposed along the central axis and within the interior cavity of the housing for conditioning fluid traversing the first flow path from a first inlet port to a first outlet port;
   iii) a second filter element disposed along the central axis and within the interior cavity of the housing for conditioning fluid traversing the second flow path from a second inlet port to a second outlet port; and
   iv) a third filter element disposed along the central axis and within the interior cavity of the housing for conditioning fluid traversing the third flow path from a third inlet port to a third outlet port, wherein the first flow path is isolated from the second and third flow paths and the second flow path is isolated from the third flow path, and wherein the housing includes two longitudinal ribs which define two longitudinal channels in the interior cavity of the housing and the second flow path traverse one of the channels and the third flow path traverses the other channel.

52. A filter cartridge assembly as recited in claim 51, wherein the proximal end of the housing includes a connector element.

53. A filter cartridge assembly as recited in claim 52, wherein the connector element includes the first inlet port and the second and third outlet ports.

54. A filter cartridge assembly as recited in claim 51, wherein the housing includes a pair of coaxially positioned peripheral walls.

55. A filter cartridge assembly as recited in claim 54, wherein a portion of each of the second and third flow paths traverse axially between the peripheral walls of the housing.

56. A filter cartridge assembly as recited in claim 51, wherein the first filter element is radially pleated filter and fluid is conditioned in the first flow path by traversing in a radially inward direction through the first filter element.

57. A filter cartridge assembly as recited in claim 51, wherein the second filter element is radially pleated filter and fluid is conditioned in the second flow path by traversing in a radially outward direction through the second filter element.

58. A filter cartridge assembly as recited in claim 51, wherein the third filter element is a disc filter and fluid is conditioned in the second flow path by traversing axially through the third filter element.

59. A filter cartridge assembly as recited in claim 51, wherein the housing further includes a second inner housing element positioned within the interior cavity of the housing and forming a second chamber for the second filter element.

60. A filter cartridge assembly as recited in claim 51, wherein the first outlet port, the second inlet port and third inlet port are located at the distal end of the housing.

61. A filter cartridge assembly as recited in claim 60, wherein the first outlet port, the second inlet port and the third inlet port are coaxially arranged.

62. A filter cartridge assembly comprising:
   i) an elongated housing having axially opposed proximal and distal ends, the housing defining an interior cavity, a central axis and first, second and third flow paths which extend from the proximal end of the housing to the distal end;
   ii) a first filter element disposed along the central axis and within the interior cavity of the housing for conditioning fluid traversing the first flow path from a first inlet port to a first outlet port;
   iii) a second filter element disposed along the central axis and within the interior cavity of the housing for conditioning fluid traversing the second flow path from a second inlet port to a second outlet port; and
   iv) a third filter element disposed along the central axis and within the interior cavity of the housing for conditioning fluid traversing the third flow path from a third inlet port to a third outlet port, wherein the first flow path is isolated from the second and third flow paths and the second flow path is isolated from the third flow path, and wherein the first outlet port, the second inlet port and third inlet port are located at the distal end of the housing.

63. A filter cartridge assembly as recited in claim 62, wherein the proximal end of the housing includes a connector element.

64. A filter cartridge assembly as recited in claim 63, wherein the connector element includes the first inlet port and the second and third outlet ports.

65. A filter cartridge assembly as recited in claim 62, wherein the housing includes a pair of coaxially positioned peripheral walls.

66. A filter cartridge assembly as recited in claim 65, wherein a portion of each of the second and third flow paths traverse axially between the peripheral walls of the housing.

67. A filter cartridge assembly as recited in claim 62, wherein the first filter element is radially pleated filter and fluid is conditioned in the first flow path by traversing in a radially inward direction through the first filter element.

68. A filter cartridge assembly as recited in claim 62, wherein the second filter element is radially pleated filter and fluid is conditioned in the second flow path by traversing in a radially outward direction through the second filter element.

69. A filter cartridge assembly as recited in claim 62, wherein the third filter element is a disc filter and fluid is conditioned in the second flow path by traversing axially through the third filter element.

70. A filter cartridge assembly as recited in claim 62, wherein the housing further includes a second inner housing element positioned within the interior cavity of the housing and forming a second chamber for the second filter element.

71. A filter cartridge assembly as recited in claim 62, wherein the housing includes two longitudinal ribs which define two longitudinal channels in the interior cavity of the housing and the second flow path traverse one of the channels and the third flow path traverses the other channel.

72. A filter cartridge assembly as recited in claim 62, wherein the first outlet port, the second inlet port and the third inlet port are coaxially arranged.

\* \* \* \* \*